United States Patent
Weser et al.

(10) Patent No.: US 9,999,582 B2
(45) Date of Patent: Jun. 19, 2018

(54) COMBINATIONS OF PRESERVATIVES FOR HAIR COLORS

(71) Applicant: Henkel AG & Co. KGaA, Duesseldorf (DE)

(72) Inventors: Gabriele Weser, Neuss (DE); Rainer Simmering, Grevenbroich (DE); Mustafa Akram, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days. days.

(21) Appl. No.: 15/379,201

(22) Filed: Dec. 14, 2016

(65) Prior Publication Data
US 2017/0172876 A1   Jun. 22, 2017

(30) Foreign Application Priority Data
Dec. 16, 2015   (DE) .................... 10 2015 225 361

(51) Int. Cl.
| | |
|---|---|
| *A61Q 5/10* | (2006.01) |
| *A61K 8/368* | (2006.01) |
| *A61K 8/36* | (2006.01) |
| *A61K 8/365* | (2006.01) |
| *A61K 8/49* | (2006.01) |
| *A61K 8/41* | (2006.01) |
| *A61K 8/34* | (2006.01) |
| *A61K 8/23* | (2006.01) |
| *A61K 8/40* | (2006.01) |
| *A61K 8/42* | (2006.01) |
| *A61K 8/44* | (2006.01) |

(52) U.S. Cl.
CPC ............... *A61K 8/368* (2013.01); *A61K 8/23* (2013.01); *A61K 8/34* (2013.01); *A61K 8/347* (2013.01); *A61K 8/36* (2013.01); *A61K 8/365* (2013.01); *A61K 8/40* (2013.01); *A61K 8/41* (2013.01); *A61K 8/42* (2013.01); *A61K 8/44* (2013.01); *A61K 8/494* (2013.01); *A61K 8/4913* (2013.01); *A61K 8/4926* (2013.01); *A61Q 5/10* (2013.01); *A61K 2800/4324* (2013.01); *A61K 2800/524* (2013.01); *A61K 2800/592* (2013.01)

(58) Field of Classification Search
CPC ........ A61K 8/368; A61K 8/36; A61K 8/4926; A61K 8/365; A61K 8/41; A61K 8/347; A61K 8/4913; A61K 8/34; A61K 8/23; A61K 8/40; A61K 8/494; A61K 8/42; A61K 8/44; A61K 2800/594; A61K 2800/592; A61Q 5/10
See application file for complete search history.

(56) References Cited

U.S. PATENT DOCUMENTS

| | | | |
|---|---|---|---|
| 2005/0166337 A1* | 8/2005 | Adam .................... | A61K 8/40 8/406 |
| 2005/0287091 A1* | 12/2005 | Kaiser .................... | A61K 8/73 424/63 |

* cited by examiner

*Primary Examiner* — Eisa B Elhilo
(74) *Attorney, Agent, or Firm* — James J. Cummings

(57) ABSTRACT

An agent for coloring keratinic fibers, particularly human hairs, includes in a cosmetic carrier
(a) at least one preservative from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate, and
(b) at least one oxidation dye precursor and/or at least one direct dye.
A second object of the present invention is a method for manufacturing a colorant of the first object of the invention.

12 Claims, No Drawings

COMBINATIONS OF PRESERVATIVES FOR HAIR COLORS

FIELD OF THE INVENTION

The present invention generally relates to preservative mixtures for use in the area of hair dyes.

BACKGROUND OF THE INVENTION

As a result of their composition, cosmetic agents can serve as a growth medium for germs and microorganisms. These germs can result in the microbial contamination of the user and alter the ingredients of the cosmetics so as to create substances having adverse effects such as sensitization or skin irritation. To avoid these undesired consequences while ensuring a certain minimum shelf life of the cosmetics, they must be preserved. Since preservatives themselves can have irritative potential, the use thereof in cosmetics is strictly regulated.

Cosmetic products for changing the hair color generally include direct dyes and/or oxidation dye precursors. During the use of direct dyes, the ready-to-use dyes are applied to the keratin fibers.

The addition of preservatives can be required especially with level 1 colorations. Level 1 colorations include no oxidation dye precursors, but rather only direct dyes. To prevent damaging the hair, there is a trend toward setting level 1 colorations to neutral to slightly acidic pH values. Particularly if no large quantities of alkalizing agents are used, level 1 colorations can be contaminated by germs. This contamination must be prevented through the addition of maximally effective and well suited preservatives.

Oxidation dye precursors are included in oxidative colorants. These are so-called developer components and coupler components, which form the actual colorants only under the influence of oxidizing agents (generally hydrogen peroxide). Oxidizing agents are characterized by long-lasting coloring results.

Oxidative colorants are usually applied in an alkaline medium and require the presence of hydrogen peroxide. Since hydrogen peroxide itself has biocidal and preserving characteristics, it is normally not necessary to also add additional preservatives to oxidative color-changing agents other than hydrogen peroxide. Under certain conditions, however, the preservation of oxidative colorants can be necessary.

Oxidative coloration takes a toll on hair, and it is for that reason that it is generally repeated only after a period of 6 to 8 weeks. Within this time period, however, the hair grows in and the non-dyed hairs become visible at the base. This difference in color between dyed and non-dyed hair is often perceived by the user as highly unattractive. One possibility for concealing these color differences is the root touch-up. In a root touch-up, only the root is dyed—for example 2 to 3 weeks after the regular dyeing of all of the hair. Since this root touch-up is performed as additional coloration between the regular whole-head coloration procedures, it constitutes an additional stress for the hair and should be as gentle as possible. Appropriately, the agents used for root touch-ups are either only direct dyes, or hydrogen peroxide is used in very small concentrations. The reduction of the concentration of the hydrogen peroxide or the complete omission thereof can render the use of additional preservatives necessary.

Moreover, products for root coloration are often packaged such that their quantity is enough for several root touch-ups. The bottle or tube containing the coloring cream is repeatedly opened and closed by the user in order to remove the portion required for the individual root treatment, thereby creating the danger of contamination of the product with germs or microorganisms. The preservation of the colorants becomes necessary for this reason as well.

It is therefore desirable to provide effective preservatives and preservative mixtures that are well suited for hair dyes. The preservatives should prevent the colonization of the colorant and the scalp with undesired germs while not or not substantially harming the natural skin flora.

Moreover, it should be possible to color the keratin fibers in bright, intense colors even when using the preservatives. Particularly, the use of the preservatives should not result in any color shifting, and reactions between colorants and the preservatives as well as the formation of undesired byproducts should also be avoided. Furthermore, the fastness characteristics of the colorations should also not be negatively affected by the use of the preservatives.

Furthermore, other desirable features and characteristics of the present invention will become apparent from the subsequent detailed description of the invention and the appended claims, taken in conjunction with this background of the invention.

BRIEF SUMMARY OF THE INVENTION

An agent for coloring keratinic fibers, particularly human hairs, including in a cosmetic carrier at least one preservative from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate; and at least one oxidation dye precursor and/or at least one direct dye.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was found that the above-described objects can be achieved with outstanding results if at least one of the preservatives or preservative mixtures described in the following is used in the colorant.

A first object of the present is a means for coloring keratinic fibers, particularly human hairs, including in a cosmetic carrier (a) at least one preservative from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3, 4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate, and (b) at least one oxidation dye precursor and/or at least one direct dye.

Keratinic fibers are understood as being wool, furs, feathers and particularly human hairs. In the present invention, the terms "keratinic fibers" and "keratin fibers" are used synonymously. In principle, however, the colorants according to the invention can also be used to color other natural fibers such as cotton, jute, sisal, linen, or silk, for example, and modified natural fibers such as regenerated cellulose, nitro-, alkyl or hydroxyalkyl or acetyl cellulose. Very especially preferably, the agents according to the invention are agents for coloring human hair.

The agents according to the invention include ingredients (a) and (b) in a cosmetic carrier, preferably in a suitable aqueous, alcoholic or aqueous/alcoholic carrier. For the purpose of hair coloration, such carriers are, for example, creams, emulsions, gels or even surfactant-containing foaming solutions such as shampoos, foaming aerosols, foam formulations or other preparations that are suitable for use on the hair.

As the first essential ingredient (a), the agents according to the invention include at least one preservative from the group consisting of sorbic acid, 2-hydroxydiphenyl, 4-hydroxybenzoic acid, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate.

Sorbic acid bears the alternative name 2,4-hexadienoic acid ((2E,4E)-hexa-2,4-dienoic acid) and has CAS number 110-44-1. The salts of sorbic acid, particularly sodium salt and potassium salt, are also included by the invention.

2-hydroxydiphenyl is alternatively referred to as biphenyl-2-ol or 2-hydroxybiphenyl or orthophenylphenol. 2-hydroxydiphenyl has CAS number 90-43-7.

4-hydroxybenzoic acid is also alternatively referred to as p-salicylic acid, p-hydroxybenzoic acid and has CAS number 99-96-7.

Dehydroacetic acid has the alternative name 3-acetyl-6-methyl-2,4(3H)-pyrandione, has CAS number 520-45-6 and has the structure (K1). The tautomeric forms of dehydroacetic acid are also included by the invention.

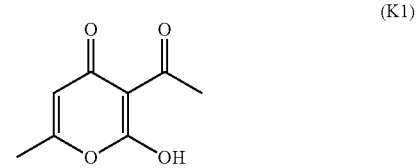

(K1)

Dibromohexamidine is also alternatively referred to as 1,6-bis(4-amidino-2-bromophenoxy)-n-hexane or as, 4'-(hexane-1,6-diyl)-bis-(3-bromobenzamidine) and has CAS number 93856-82-7. Dibromohexamidine has the structure (K2).

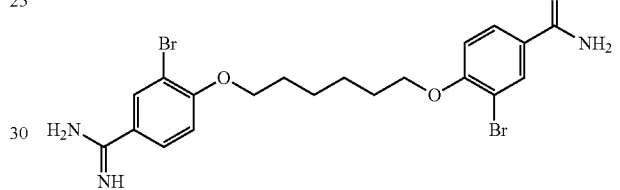

(K2)

10-undecylenic acid bears the alternative name undec-10-enic acid or 10-undecanoic acid and has CAS number 112-38-9. 10-undecylenic acid has the structure of formula (K3). The salts of 10-undecylenic acid, particularly sodium salt and potassium salt, are also included by the invention.

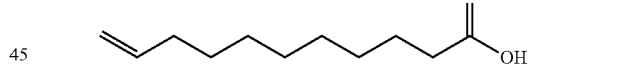

(K3)

Hexamidine is alternatively also referred to as hexetidine or 1,3-bis(2-ethylhexyl)-5-methylhexahydropyrimidine-5-amine. Hexamidine or hexetidine has CAS number 141-94-6. Hexamidine or hexetidine has the structure of formula (K4).

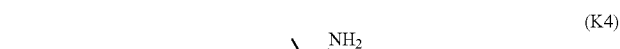

(K4)

Triclocarban also bears the alternative names 3,4,4'-trichlorocarbanilide or 3-(4-chlorophenyl)-1-(3,4-dichlorophenyl) urea and has CAS number 101-20-2. Triclocarban has the structure of formula (K5).

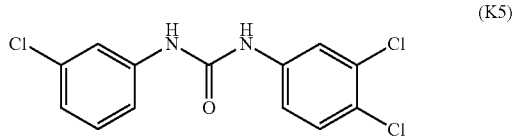 [SMILES: O=C(Nc1cccc(Cl)c1)Nc1ccc(Cl)c(Cl)c1]
(K5)

Triclosan or triclosanum is alternatively also referred to as 5-Chloro-2-(2,4-dichlorophenoxy)-phenol. Triclosan or triclosanum has CAS number 3380-34-5. Triclosan or triclosanum has the structure of formula (K6)

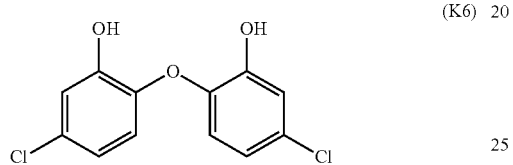
(K6)

4-chloro-3,4-dimethylphenol is also referred to as chloroxylenol and has CAS number 88-04-0.

Imidazolidinyl urea is alternatively also referred to as N,N'-methylenebis[N'-(3-hydroxymethyl-2,5-dioxo-4-imidazolidinyl)urea]. Imidazolidinyl urea has CAS number 39236-46-9 and has the structure of formula (K7).

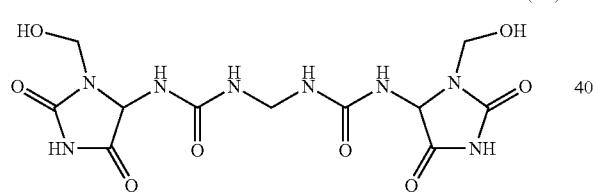
(K7)

Hexamethylenetetramine is also referred to as urotropin or 1,3,5,7-tetraaza adamantane. Hexamethylenetetramine has CAS number 100-97-0.

1-(4-chlorophenoxy)-1-(imidazole-1-yl)-3,3-dimethyl-2-butanone is alternatively also referred to as climbazole, has CAS number 38083-17-9 and a structure of formula (K8). The structure K8 comprises two enantiomeric forms. Both enantiomers as well as the mixture of the two enantiomers are also included by the invention.

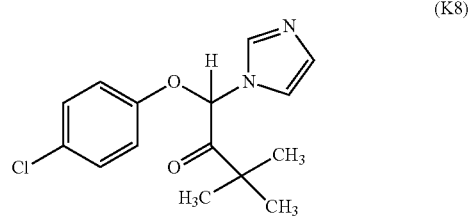 [SMILES: CC(C)(C)C(=O)C(Oc1ccc(Cl)cc1)n1ccnc1]
(K8)

1,3-bis-(hydroxymethyl)-5,5-dimethyl-2,4-imidazolidinedione is also referred to as DMDM hydantoin, has CAS number 6440-58-0 and has the structure of formula (K9).

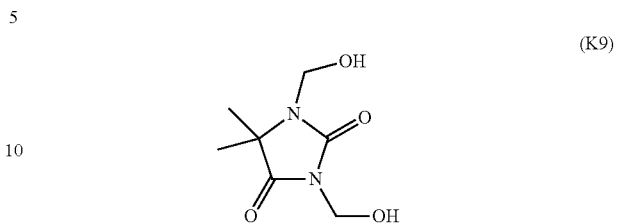
(K9)

1-hydroxy-4-methyl-6-(2,4,4-trimethylpentyl)-2-pyridone has the alternative names 1-hydroxy-4-methyl-6-(2,4,4-trimethylpentyl)pyridine-2(1H)-on, octopirox and piroctone olamine and has CAS number 68890-66-4. Especially preferably, this preservative is used in the form of its 1:1 adduct with 1-amino ethanol. 1-hydroxy-4-methyl-6-(2,4,4-trimethylpentyl)-2-pyridone (in the form of its ethanolamine adduct) has the structure of formula (K10).

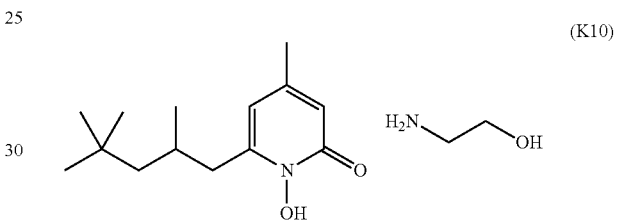
(K10)

Bromochlorophene bears the alternative name 2,2'-methylenebis-(6-bromo-4-chlorophenol) and has CAS number 15435-29-7. Bromochlorophene has the structure of formula (K11).

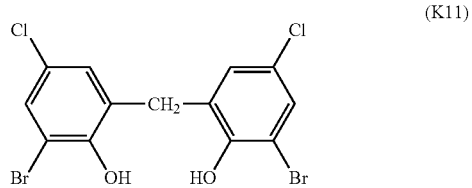 [SMILES: Oc1c(Br)cc(Cl)cc1Cc1cc(Cl)cc(Br)c1O]
(K11)

3-methyl-4-(1-methylethyl)phenol bears the alternative names o-cymen-5-ol, p-thymol, biosol and 1-hydroxy-3-methyl-4-isopropylbenzene and has CAS number 3228-02-2.

5-chloro-2-methyl-3(2H)-isothiazolone is alternatively also referred to as 5-chloro-2-methyl-4-isothiazoline-3-on or chloromethylisothiazolone, has CAS number 26172-55-4 and has the structure of formula (K12).

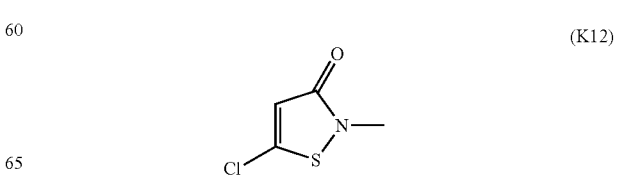
(K12)

2-benzyl-4-chlorophenol is alternatively also referred to as chlorophenum or chlorphen and has CAS number 120-32-1.

2-chloroacetamide bears the alternative name chloroacetic acid amide and has CAS number 79-07-2.

Chlorohexidine is alternatively also referred to as 1,1'-hexamethylene-bis[5-(4-chlorophenyl)biguanide] and has CAS number 55-56-1. Chlorohexidine has the structure of formula (K13).

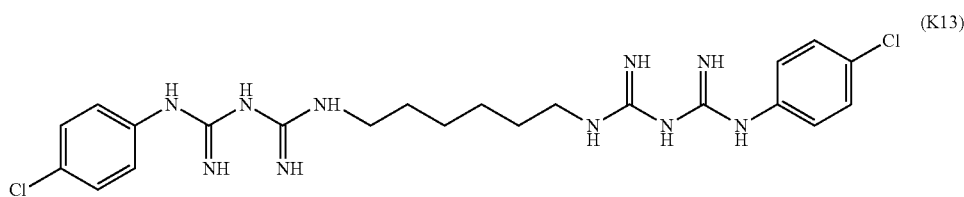 [SMILES: N=C(NCCCCCCNC(=N)NC(=N)Nc1ccc(Cl)cc1)NC(=N)Nc1ccc(Cl)cc1]

(K13)

4,4-dimethyl-1,3-oxazolidine has CAS number 51200-87-4.

1-phenoxy-propane-2-ol is alternatively also referred to as phenyl-β-hydroxypropyl ether, 1-phenoxy-2-propanol, phenoxyisopropanol, propylene phenoxetol, 2-phenoxy-1-methylethanol or propylene glycol 1-phenyl ether and has CAS number 770-35-4.

Hexamidine is alternatively also referred to as hexamidinum or 1,6-bis(4-amidinophenoxy)-n-hexane or 4,4'-[hexane-1,6-diylbis(oxy)]dibenzene carboximidamide and has CAS number 3811-75-4. Hexamidine has the structure of formula (K14).

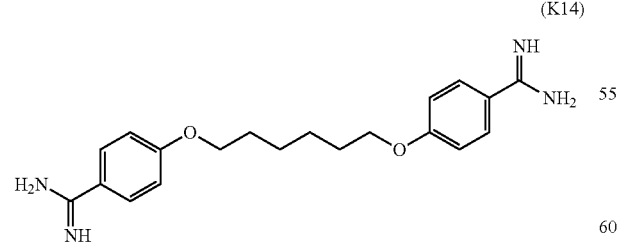

(K14)

5-ethyl-1-aza-3,7-dioxabicyclo-[3.3.0]-octane is alternatively also referred to as 5-ethyl-3,7-dioxa-1-azabicyclo-[3.3.0]octane or dihydro-7a-ethyloxazolo[3,4-c]oxazol, has CAS number 7747-35-5 and has the structure of formula (K15).

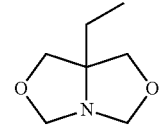

(K15)

Chlorphenesin is alternatively also referred to as (3-(4-chlorophenoxy)-2-hydroxypropyl)carbamate and has CAS number 886-74-8. Chlorphenesin has the structure of formula (K16).

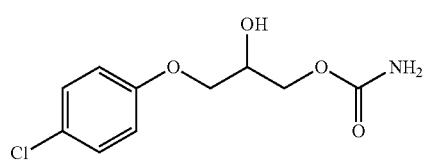

(K16)

Sodium hydroxymethyl amino acetate is alternatively also referred to as sodium-N-(hydroxymethyl)glycinate or sodium-N-(hydroxymethyl)glycinate, has CAS number 70161-44-3 and has the structure of formula (K17).

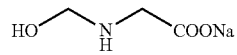

(K17)

Benzyl hemiformal is alternatively also referred to as (benzyloxy)methanol and has CAS number 14548-60-8.

3-iodo-2-propinyl butylcarbamate is alternatively also referred to as 3-iodopropargyl-N-butylcarbamate or biodocarb and has CAS number 55406-53-6. 3-iodo-2-propynyl butylcarbamate has the structure of formula (K18).

(K18)

Methylisothiazolinone is alternatively also referred to as 2-methyl-2H-isothiazole-3-on and has CAS number 2682-20-4.

Ethyl lauroyl arginate is alternatively also referred to as ethyl-Nα-dodecanoyl-L-arginate hydrochloride or monohydrochloride of L-arginine or Na-lauroyl ethyl ester and has CAS number 60372-77-2. Ethyl lauroyl arginate has the structure of formula (K19) and can be used either as a free compound or in the form of its hydrochloride salt.

(K19)

The preservatives according to the invention (a) can interact in a synergistic manner, whereby through the use of a combination of at least two preservatives from group (a), a preservative effect is produced that is greater than if an equally large quantity of a single preservative is used.

In a very especially preferred embodiment, the agent according to the invention for coloring keratin fibers therefore includes at least two preservatives from the group of sorbic acid, 2-hydroxydiphenyl, 4-hydroxybenzoic acid, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate.

In an especially preferred embodiment, an agent according to the invention for coloring keratin fibers is characterized in that it includes
(a) at least two preservatives from the group of sorbic acid, 2-hydroxydiphenyl, 4-hydroxybenzoic acid, dehydroacetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate.

In an especially preferred embodiment, an agent according to the invention for coloring keratin fibers is characterized in that it includes
(a) sorbic acid and 2-hydroxydiphenyl and
(b) at least one oxidation dye precursor and/or one direct dye.

In an especially preferred embodiment, an agent according to the invention for coloring keratin fibers is characterized in that it includes
(a) sorbic acid and 4-hydroxybenzoic acid, and
(b) at least one oxidation dye precursor and/or one direct dye.

In an especially preferred embodiment, an agent according to the invention for coloring keratin fibers is characterized in that it includes
(a) sorbic acid and dehydroacetic acid and
(b) at least one oxidation dye precursor and/or one direct dye.

In an especially preferred embodiment, an agent according to the invention for coloring keratin fibers is characterized in that it includes
(a) sorbic acid and dibromohexamidine and
(b) at least one oxidation dye precursor and/or one direct dye.

In an especially preferred embodiment, an agent according to the invention for coloring keratin fibers is characterized in that it includes
(a) sorbic acid and 10-undecylenic acid and
(b) at least one oxidation dye precursor and/or one direct dye.

In an especially preferred embodiment, an agent according to the invention for coloring keratin fibers is characterized in that it includes
(a) sorbic acid and hexetidine and
(b) at least one oxidation dye precursor and/or one direct dye.

In an especially preferred embodiment, an agent according to the invention for coloring keratin fibers is characterized in that it includes
(a) sorbic acid and trichlorocarban and
(b) at least one oxidation dye precursor and/or one direct dye.

In an especially preferred embodiment, an agent according to the invention for coloring keratin fibers is characterized in that it includes
(a) sorbic acid and triclosan and
(b) at least one oxidation dye precursor and/or one direct dye.

In an especially preferred embodiment, an agent according to the invention for coloring keratin fibers is characterized in that it includes
(a) sorbic acid and 4-chloro-3,4-dimethylphenol and
(b) at least one oxidation dye precursor and/or one direct dye.

In an especially preferred embodiment, an agent according to the invention for coloring keratin fibers is characterized in that it includes
(a) sorbic acid and imidazolidinyl urea and
(b) at least one oxidation dye precursor and/or one direct dye.

In an especially preferred embodiment, an agent according to the invention for coloring keratin fibers is characterized in that it includes (a) sorbic acid and hexamethylenetetramine and
(b) at least one oxidation dye precursor and/or one direct dye.

In an especially preferred embodiment, an agent according to the invention for coloring keratin fibers is characterized in that it includes
(a) sorbic acid and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) sorbic acid and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) sorbic acid and 1-hydroxy-4-methyl-6-(2,4,4-trimethyl-pentyl)-2-pyridone and
(b) at least one oxidation dye precursor and/or one direct dye.

In an especially preferred embodiment, an agent according to the invention for coloring keratin fibers is characterized in that it includes
(a) sorbic acid and bromochlorophene and
(b) at least one oxidation dye precursor and/or one direct dye.

In an especially preferred embodiment, an agent according to the invention for coloring keratin fibers is characterized in that it includes
(a) sorbic acid and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) sorbic acid and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) sorbic acid and 2-benzyl-4-chlorophenol and
(b) at least one oxidation dye precursor and/or one direct dye.

In an especially preferred embodiment, an agent according to the invention for coloring keratin fibers is characterized in that it includes
(a) sorbic acid and 2-chloroacetamide and
(b) at least one oxidation dye precursor and/or one direct dye.

In an especially preferred embodiment, an agent according to the invention for coloring keratin fibers is characterized in that it includes
(a) sorbic acid and chlorohexidine and
(b) at least one oxidation dye precursor and/or one direct dye.

In an especially preferred embodiment, an agent according to the invention for coloring keratin fibers is characterized in that it includes
(a) sorbic acid and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) sorbic acid and 1-phenoxy-propane-2-ol and
(b) at least one oxidation dye precursor and/or one direct dye.

In an especially preferred embodiment, an agent according to the invention for coloring keratin fibers is characterized in that it includes
(a) sorbic acid and hexamidine and
(b) at least one oxidation dye precursor and/or one direct dye.

In an especially preferred embodiment, an agent according to the invention for coloring keratin fibers is characterized in that it includes
(a) sorbic acid and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) sorbic acid and chlorphenesin and
(b) at least one oxidation dye precursor and/or one direct dye.

In an especially preferred embodiment, an agent according to the invention for coloring keratin fibers is characterized in that it includes
(a) sorbic acid and sodium hydroxymethyl amino acetate and
(b) at least one oxidation dye precursor and/or one direct dye.

In an especially preferred embodiment, an agent according to the invention for coloring keratin fibers is characterized in that it includes
(a) sorbic acid and benzyl hemiformal and
(b) at least one oxidation dye precursor and/or one direct dye.

In an especially preferred embodiment, an agent according to the invention for coloring keratin fibers is characterized in that it includes
(a) sorbic acid and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) sorbic acid and methylisothiazolinone and
(b) at least one oxidation dye precursor and/or one direct dye.

In an especially preferred embodiment, an agent according to the invention for coloring keratin fibers is characterized in that it includes
(a) sorbic acid and ethyl lauroyl arginate and
(b) at least one oxidation dye precursor and/or one direct dye.

In an especially preferred embodiment, an agent according to the invention for coloring keratin fibers is characterized in that it includes
(a) 2-hydroxydiphenyl and 4-hydroxybenzoic acid, and
(b) at least one oxidation dye precursor and/or one direct dye.

In an especially preferred embodiment, an agent according to the invention for coloring keratin fibers is characterized in that it includes
(a) 2-hydroxydiphenyl and dehydroacetic acid and
(b) at least one oxidation dye precursor and/or one direct dye.

In an especially preferred embodiment, an agent according to the invention for coloring keratin fibers is characterized in that it includes
(a) 2-hydroxydiphenyl and dibromohexamidine and
(b) at least one oxidation dye precursor and/or one direct dye.

In an especially preferred embodiment, an agent according to the invention for coloring keratin fibers is characterized in that it includes
(a) 2-hydroxydiphenyl and 10-undecylenic acid and
(b) at least one oxidation dye precursor and/or one direct dye.

In an especially preferred embodiment, an agent according to the invention for coloring keratin fibers is characterized in that it includes
(a) 2-hydroxydiphenyl and hexetidine and
(b) at least one oxidation dye precursor and/or one direct dye.

In an especially preferred embodiment, an agent according to the invention for coloring keratin fibers is characterized in that it includes
(a) 2-hydroxydiphenyl and trichlorocarban and
(b) at least one oxidation dye precursor and/or one direct dye.

In an especially preferred embodiment, an agent according to the invention for coloring keratin fibers is characterized in that it includes
(a) 2-hydroxydiphenyl and triclosan and
(b) at least one oxidation dye precursor and/or one direct dye.

In an especially preferred embodiment, an agent according to the invention for coloring keratin fibers is characterized in that it includes
(a) 2-hydroxydiphenyl and 4-chloro-3,4-dimethylphenol and
(b) at least one oxidation dye precursor and/or one direct dye.

In an especially preferred embodiment, an agent according to the invention for coloring keratin fibers is characterized in that it includes
(a) 2-hydroxydiphenyl and imidazolidinyl urea and
(b) at least one oxidation dye precursor and/or one direct dye.

In an especially preferred embodiment, an agent according to the invention for coloring keratin fibers is characterized in that it includes
(a) 2-hydroxydiphenyl and hexamethylenetetramine and
(b) at least one oxidation dye precursor and/or one direct dye.

In an especially preferred embodiment, an agent according to the invention for coloring keratin fibers is characterized in that it includes
(a) 2-hydroxydiphenyl and 1-(4-chloro phenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) 2-hydroxydiphenyl and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) 2-hydroxydiphenyl and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) 2-hydroxydiphenyl and bromochlorophene and
(b) at least one oxidation dye precursor and/or one direct dye.

In an especially preferred embodiment, an agent according to the invention for coloring keratin fibers is characterized in that it includes
(a) 2-hydroxydiphenyl and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) 2-hydroxydiphenyl and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 2-hydroxydiphenyl and 2-benzyl-4-chlorophenol and
(b) at least one oxidation dye precursor and/or one direct dye.

In an especially preferred embodiment, an agent according to the invention for coloring keratin fibers is characterized in that it includes
(a) 2-hydroxydiphenyl and 2-chloroacetamide and
(b) at least one oxidation dye precursor and/or one direct dye.

In an especially preferred embodiment, an agent according to the invention for coloring keratin fibers is characterized in that it includes
(a) 2-hydroxydiphenyl and chlorohexidine and
(b) at least one oxidation dye precursor and/or one direct dye.

In an especially preferred embodiment, an agent according to the invention for coloring keratin fibers is characterized in that it includes
(a) 2-hydroxydiphenyl and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 2-hydroxydiphenyl and 1-phenoxy-propane-2-ol, hexamidine and
(b) at least one oxidation dye precursor and/or one direct dye.

In an especially preferred embodiment, an agent according to the invention for coloring keratin fibers is characterized in that it includes (a) 2-hydroxydiphenyl and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 2-hydroxydiphenyl and chlorphenesin and
(b) at least one oxidation dye precursor and/or one direct dye.

In an especially preferred embodiment, an agent according to the invention for coloring keratin fibers is characterized in that it includes
(a) 2-hydroxydiphenyl and sodium hydroxymethyl amino acetate and
(b) at least one oxidation dye precursor and/or one direct dye.

In an especially preferred embodiment, an agent according to the invention for coloring keratin fibers is characterized in that it includes
(a) 2-hydroxydiphenyl and benzyl hemiformal and
(b) at least one oxidation dye precursor and/or one direct dye.

In an especially preferred embodiment, an agent according to the invention for coloring keratin fibers is characterized in that it includes
(a) 2-hydroxydiphenyl and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 2-hydroxydiphenyl and methylisothiazolinone and
(b) at least one oxidation dye precursor and/or one direct dye.

In an especially preferred embodiment, an agent according to the invention for coloring keratin fibers is characterized in that it includes
(a) 2-hydroxydiphenyl and ethyl lauroyl arginate and
(b) at least one oxidation dye precursor and/or one direct dye.

In an especially preferred embodiment, an agent according to the invention for coloring keratin fibers is characterized in that it includes
(a) 4-hydroxybenzoic acid and dehydroacetic acid and
(b) at least one oxidation dye precursor and/or one direct dye.

In an especially preferred embodiment, an agent according to the invention for coloring keratin fibers is characterized in that it includes
(a) 4-hydroxybenzoic acid and dibromohexamidine and
(b) at least one oxidation dye precursor and/or one direct dye.

In an especially preferred embodiment, an agent according to the invention for coloring keratin fibers is characterized in that it includes
(a) 4-hydroxybenzoic acid and 10-undecylenic acid and
(b) at least one oxidation dye precursor and/or one direct dye.

In an especially preferred embodiment, an agent according to the invention for coloring keratin fibers is characterized in that it includes
(a) 4-hydroxybenzoic acid and hexetidine and
(b) at least one oxidation dye precursor and/or one direct dye.

In an especially preferred embodiment, an agent according to the invention for coloring keratin fibers is characterized in that it includes
(a) 4-hydroxybenzoic acid and trichlorocarban and
(b) at least one oxidation dye precursor and/or one direct dye.

In an especially preferred embodiment, an agent according to the invention for coloring keratin fibers is characterized in that it includes
(a) 4-hydroxybenzoic acid and triclosan and
(b) at least one oxidation dye precursor and/or one direct dye.

In an especially preferred embodiment, an agent according to the invention for coloring keratin fibers is characterized in that it includes
(a) 4-hydroxybenzoic acid and 4-chloro-3,4-dimethylphenol and
(b) at least one oxidation dye precursor and/or one direct dye.

In an especially preferred embodiment, an agent according to the invention for coloring keratin fibers is characterized in that it includes
(a) 4-hydroxybenzoic acid and imidazolidinyl urea and
(b) at least one oxidation dye precursor and/or one direct dye.

In an especially preferred embodiment, an agent according to the invention for coloring keratin fibers is characterized in that it includes
(a) 4-hydroxybenzoic acid and hexamethylenetetramine and
(b) at least one oxidation dye precursor and/or one direct dye.

In an especially preferred embodiment, an agent according to the invention for coloring keratin fibers is characterized in that it includes
(a) 4-hydroxybenzoic acid and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) 4-hydroxybenzoic acid and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) 4-hydroxybenzoic acid and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) 4-hydroxybenzoic acid and bromochlorophene and
(b) at least one oxidation dye precursor and/or one direct dye.

In an especially preferred embodiment, an agent according to the invention for coloring keratin fibers is characterized in that it includes
(a) 4-hydroxybenzoic acid and 3-methyl-4-(1-methylethyl)phenol and (b) at least one oxidation dye precursor and/or one direct dye.

In an especially preferred embodiment, an agent according to the invention for coloring keratin fibers is characterized in that it includes
(a) 4-hydroxybenzoic acid and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 4-hydroxybenzoic acid and 2-benzyl-4-chlorophenol and
(b) at least one oxidation dye precursor and/or one direct dye.

In an especially preferred embodiment, an agent according to the invention for coloring keratin fibers is characterized in that it includes
(a) 4-hydroxybenzoic acid and 2-chloroacetamide and
(b) at least one oxidation dye precursor and/or one direct dye.

In an especially preferred embodiment, an agent according to the invention for coloring keratin fibers is characterized in that it includes
(a) 4-hydroxybenzoic acid and chlorohexidine and
(b) at least one oxidation dye precursor and/or one direct dye.

In an especially preferred embodiment, an agent according to the invention for coloring keratin fibers is characterized in that it includes
(a) 4-hydroxybenzoic acid and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 2-hydroxybenzoic acid and 1-phenoxy-propane-2-ol and
(b) at least one oxidation dye precursor and/or one direct dye.

In an especially preferred embodiment, an agent according to the invention for coloring keratin fibers is characterized in that it includes
(a) 4-hydroxybenzoic acid and hexamidine and
(b) at least one oxidation dye precursor and/or one direct dye.

In an especially preferred embodiment, an agent according to the invention for coloring keratin fibers is characterized in that it includes
(a) 4-hydroxybenzoic acid and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 4-hydroxybenzoic acid and chlorphenesin and
(b) at least one oxidation dye precursor and/or one direct dye.

In an especially preferred embodiment, an agent according to the invention for coloring keratin fibers is characterized in that it includes
(a) 4-hydroxybenzoic acid and sodium hydroxymethyl amino acetate and
(b) at least one oxidation dye precursor and/or one direct dye.

In an especially preferred embodiment, an agent according to the invention for coloring keratin fibers is characterized in that it includes
(a) 4-hydroxybenzoic acid and benzyl hemiformal and
(b) at least one oxidation dye precursor and/or one direct dye.

In an especially preferred embodiment, an agent according to the invention for coloring keratin fibers is characterized in that it includes
(a) 4-hydroxybenzoic acid and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 4-hydroxybenzoic acid and methylisothiazolinone and
(b) at least one oxidation dye precursor and/or one direct dye.

In an especially preferred embodiment, an agent according to the invention for coloring keratin fibers is characterized in that it includes
(a) 4-hydroxybenzoic acid and ethyl lauroyl arginate and
(b) at least one oxidation dye precursor and/or one direct dye.

In an especially preferred embodiment, an agent according to the invention for coloring keratin fibers is characterized in that it includes
(a) dehydroacetic acid and dibromohexamidine and
(b) at least one oxidation dye precursor and/or one direct dye.

In an especially preferred embodiment, an agent according to the invention for coloring keratin fibers is characterized in that it includes
(a) dehydroacetic acid and 10-undecylenic acid and
(b) at least one oxidation dye precursor and/or one direct dye.

In an especially preferred embodiment, an agent according to the invention for coloring keratin fibers is characterized in that it includes
(a) dehydroacetic acid and hexetidine and
(b) at least one oxidation dye precursor and/or one direct dye.

In an especially preferred embodiment, an agent according to the invention for coloring keratin fibers is characterized in that it includes
(a) dehydroacetic acid and trichlorocarban and
(b) at least one oxidation dye precursor and/or one direct dye.

In an especially preferred embodiment, an agent according to the invention for coloring keratin fibers is characterized in that it includes
(a) dehydroacetic acid and triclosan and
(b) at least one oxidation dye precursor and/or one direct dye.

In an especially preferred embodiment, an agent according to the invention for coloring keratin fibers is characterized in that it includes
(a) dehydroacetic acid and 4-chloro-3,4-dimethylphenol and
(b) at least one oxidation dye precursor and/or one direct dye.

In an especially preferred embodiment, an agent according to the invention for coloring keratin fibers is characterized in that it includes
(a) dehydroacetic acid and imidazolidinyl urea and
(b) at least one oxidation dye precursor and/or one direct dye.

In an especially preferred embodiment, an agent according to the invention for coloring keratin fibers is characterized in that it includes
(a) dehydroacetic acid and hexamethylenetetramine and
(b) at least one oxidation dye precursor and/or one direct dye.

In an especially preferred embodiment, an agent according to the invention for coloring keratin fibers is characterized in that it includes
(a) dehydroacetic acid and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) dehydroacetic acid and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) dehydroacetic acid and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) dehydroacetic acid and bromochlorophene and
(b) at least one oxidation dye precursor and/or one direct dye.

In an especially preferred embodiment, an agent according to the invention for coloring keratin fibers is characterized in that it includes
(a) dehydroacetic acid and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) dehydroacetic acid and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) dehydroacetic acid and 2-benzyl-4-chlorophenol and
(b) at least one oxidation dye precursor and/or one direct dye.

In an especially preferred embodiment, an agent according to the invention for coloring keratin fibers is characterized in that it includes
(a) dehydroacetic acid and 2-chloroacetamide and
(b) at least one oxidation dye precursor and/or one direct dye.

In an especially preferred embodiment, an agent according to the invention for coloring keratin fibers is characterized in that it includes
(a) dehydroacetic acid and chlorohexidine and
(b) at least one oxidation dye precursor and/or one direct dye.

In an especially preferred embodiment, an agent according to the invention for coloring keratin fibers is characterized in that it includes
(a) dehydroacetic acid and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) dehydroacetic acid and 1-phenoxy-propane-2-ol and
(b) at least one oxidation dye precursor and/or one direct dye.

In an especially preferred embodiment, an agent according to the invention for coloring keratin fibers is characterized in that it includes
(a) dehydroacetic acid and hexamidine and
(b) at least one oxidation dye precursor and/or one direct dye.

In an especially preferred embodiment, an agent according to the invention for coloring keratin fibers is characterized in that it includes
(a) dehydroacetic acid and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) dehydroacetic acid and chlorphenesin and
(b) at least one oxidation dye precursor and/or one direct dye.

In an especially preferred embodiment, an agent according to the invention for coloring keratin fibers is characterized in that it includes
(a) dehydroacetic acid and sodium hydroxymethyl amino acetate and
(b) at least one oxidation dye precursor and/or one direct dye.

In an especially preferred embodiment, an agent according to the invention for coloring keratin fibers is characterized in that it includes
(a) dehydroacetic acid and benzyl hemiformal and
(b) at least one oxidation dye precursor and/or one direct dye.

In an especially preferred embodiment, an agent according to the invention for coloring keratin fibers is characterized in that it includes
(a) dehydroacetic acid and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) dehydroacetic acid and methylisothiazolinone and
(b) at least one oxidation dye precursor and/or one direct dye.

In an especially preferred embodiment, an agent according to the invention for coloring keratin fibers is characterized in that it includes
(a) dehydroacetic acid and ethyl lauroyl arginate and
(b) at least one oxidation dye precursor and/or one direct dye.

In an especially preferred embodiment, an agent according to the invention for coloring keratin fibers is characterized in that it includes
(a) dibromohexamidine and 10-undecylenic acid and
(b) at least one oxidation dye precursor and/or one direct dye.

In an especially preferred embodiment, an agent according to the invention for coloring keratin fibers is characterized in that it includes
(a) dibromohexamidine and hexetidine and
(b) at least one oxidation dye precursor and/or one direct dye.

In an especially preferred embodiment, an agent according to the invention for coloring keratin fibers is characterized in that it includes
(a) dibromohexamidine and trichlorocarban and
(b) at least one oxidation dye precursor and/or one direct dye.

In an especially preferred embodiment, an agent according to the invention for coloring keratin fibers is characterized in that it includes
(a) dibromohexamidine and triclosan and
(b) at least one oxidation dye precursor and/or one direct dye.

In an especially preferred embodiment, an agent according to the invention for coloring keratin fibers is characterized in that it includes
(a) dibromohexamidine and 4-chloro-3,4-dimethylphenol and
(b) at least one oxidation dye precursor and/or one direct dye.

In an especially preferred embodiment, an agent according to the invention for coloring keratin fibers is characterized in that it includes
(a) dibromohexamidine and imidazolidinyl urea and
(b) at least one oxidation dye precursor and/or one direct dye.

In an especially preferred embodiment, an agent according to the invention for coloring keratin fibers is characterized in that it includes
(a) dibromohexamidine and hexamethylenetetramine and
(b) at least one oxidation dye precursor and/or one direct dye.

In an especially preferred embodiment, an agent according to the invention for coloring keratin fibers is characterized in that it includes
(a) dibromohexamidine and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) dibromohexamidine and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) dibromohexamidine and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) dibromohexamidine and bromochlorophene and
(b) at least one oxidation dye precursor and/or one direct dye.

In an especially preferred embodiment, an agent according to the invention for coloring keratin fibers is characterized in that it includes
(a) dibromohexamidine and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) dibromohexamidine and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) dibromohexamidine and 2-benzyl-4-chlorophenol and
(b) at least one oxidation dye precursor and/or one direct dye.

In an especially preferred embodiment, an agent according to the invention for coloring keratin fibers is characterized in that it includes
(a) dibromohexamidine and 2-chloroacetamide and
(b) at least one oxidation dye precursor and/or one direct dye.

In an especially preferred embodiment, an agent according to the invention for coloring keratin fibers is characterized in that it includes
(a) dibromohexamidine and chlorohexidine and
(b) at least one oxidation dye precursor and/or one direct dye.

In an especially preferred embodiment, an agent according to the invention for coloring keratin fibers is characterized in that it includes
(a) dibromohexamidine and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) dibromohexamidine and 1-phenoxy-propane-2-ol and
(b) at least one oxidation dye precursor and/or one direct dye.

In an especially preferred embodiment, an agent according to the invention for coloring keratin fibers is characterized in that it includes
(a) dibromohexamidine and hexamidine and
(b) at least one oxidation dye precursor and/or one direct dye.

In an especially preferred embodiment, an agent according to the invention for coloring keratin fibers is characterized in that it includes
(a) dibromohexamidine and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes (a) dibromohexamidine and chlorphenesin and
(b) at least one oxidation dye precursor and/or one direct dye.

In an especially preferred embodiment, an agent according to the invention for coloring keratin fibers is characterized in that it includes
(a) dibromohexamidine and sodium hydroxymethyl amino acetate and
(b) at least one oxidation dye precursor and/or one direct dye.

In an especially preferred embodiment, an agent according to the invention for coloring keratin fibers is characterized in that it includes
(a) dibromohexamidine and benzyl hemiformal and
(b) at least one oxidation dye precursor and/or one direct dye.

In an especially preferred embodiment, an agent according to the invention for coloring keratin fibers is characterized in that it includes
(a) dibromohexamidine and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) dibromohexamidine and methylisothiazolinone and
(b) at least one oxidation dye precursor and/or one direct dye.

In an especially preferred embodiment, an agent according to the invention for coloring keratin fibers is characterized in that it includes
(a) dibromohexamidine and ethyl lauroyl arginate and
(b) at least one oxidation dye precursor and/or one direct dye.

In an especially preferred embodiment, an agent according to the invention for coloring keratin fibers is characterized in that it includes
(a) 10-undecylenic acid and hexetidine and
(b) at least one oxidation dye precursor and/or one direct dye.

In an especially preferred embodiment, an agent according to the invention for coloring keratin fibers is characterized in that it includes
(a) 10-undecylenic acid and trichlorocarban and
(b) at least one oxidation dye precursor and/or one direct dye.

In an especially preferred embodiment, an agent according to the invention for coloring keratin fibers is characterized in that it includes
(a) 10-undecylenic acid and triclosan and
(b) at least one oxidation dye precursor and/or one direct dye.

In an especially preferred embodiment, an agent according to the invention for coloring keratin fibers is characterized in that it includes
(a) 10-undecylenic acid and 4-chloro-3,4-dimethylphenol and
(b) at least one oxidation dye precursor and/or one direct dye.

In an especially preferred embodiment, an agent according to the invention for coloring keratin fibers is characterized in that it includes
(a) 10-undecylenic acid and imidazolidinyl urea and
(b) at least one oxidation dye precursor and/or one direct dye.

In an especially preferred embodiment, an agent according to the invention for coloring keratin fibers is characterized in that it includes
(a) 10-undecylenic acid and hexamethylenetetramine and
(b) at least one oxidation dye precursor and/or one direct dye.

In an especially preferred embodiment, an agent according to the invention for coloring keratin fibers is characterized in that it includes
(a) 10-undecylenic acid and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) 10-undecylenic acid and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) 10-undecylenic acid and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) 10-undecylenic acid and bromochlorophene and
(b) at least one oxidation dye precursor and/or one direct dye.

In an especially preferred embodiment, an agent according to the invention for coloring keratin fibers is characterized in that it includes
(a) 10-undecylenic acid and 3-methyl-4-(1-methylethyl) phenol and
(b) at least one oxidation dye precursor and/or one direct dye.

In an especially preferred embodiment, an agent according to the invention for coloring keratin fibers is characterized in that it includes
(a) 10-undecylenic acid and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 10-undecylenic acid and 2-benzyl-4-chlorophenol and
(b) at least one oxidation dye precursor and/or one direct dye.

In an especially preferred embodiment, an agent according to the invention for coloring keratin fibers is characterized in that it includes
(a) 10-undecylenic acid and 2-chloroacetamide and
(b) at least one oxidation dye precursor and/or one direct dye.

In an especially preferred embodiment, an agent according to the invention for coloring keratin fibers is characterized in that it includes
(a) 10-undecylenic acid and chlorohexidine and
(b) at least one oxidation dye precursor and/or one direct dye.

In an especially preferred embodiment, an agent according to the invention for coloring keratin fibers is characterized in that it includes
(a) 10-undecylenic acid and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 2-undecylenic acid and 1-phenoxy-propane-2-ol and
(b) at least one oxidation dye precursor and/or one direct dye.

In an especially preferred embodiment, an agent according to the invention for coloring keratin fibers is characterized in that it includes
(a) 10-undecylenic acid and hexamidine and
(b) at least one oxidation dye precursor and/or one direct dye.

In an especially preferred embodiment, an agent according to the invention for coloring keratin fibers is characterized in that it includes
(a) 10-undecylenic acid and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 10-undecylenic acid and chlorphenesin and
(b) at least one oxidation dye precursor and/or one direct dye.

In an especially preferred embodiment, an agent according to the invention for coloring keratin fibers is characterized in that it includes
(a) 10-undecylenic acid and sodium hydroxymethyl amino acetate and
(b) at least one oxidation dye precursor and/or one direct dye.

In an especially preferred embodiment, an agent according to the invention for coloring keratin fibers is characterized in that it includes
(a) 10-undecylenic acid and benzyl hemiformal and
(b) at least one oxidation dye precursor and/or one direct dye.

In an especially preferred embodiment, an agent according to the invention for coloring keratin fibers is characterized in that it includes
(a) 10-undecylenic acid and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 10-undecylenic acid and methylisothiazolinone and
(b) at least one oxidation dye precursor and/or one direct dye.

In an especially preferred embodiment, an agent according to the invention for coloring keratin fibers is characterized in that it includes
(a) 10-undecylenic acid and ethyl lauroyl arginate and
(b) at least one oxidation dye precursor and/or one direct dye.

In an especially preferred embodiment, an agent according to the invention for coloring keratin fibers is characterized in that it includes
(a) hexetidine and trichlorocarban and
(b) at least one oxidation dye precursor and/or one direct dye.

In an especially preferred embodiment, an agent according to the invention for coloring keratin fibers is characterized in that it includes
(a) hexetidine and triclosan and
(b) at least one oxidation dye precursor and/or one direct dye.

In an especially preferred embodiment, an agent according to the invention for coloring keratin fibers is characterized in that it includes
(a) hexetidine and 4-chloro-3,4-dimethylphenol and
(b) at least one oxidation dye precursor and/or one direct dye.

In an especially preferred embodiment, an agent according to the invention for coloring keratin fibers is characterized in that it includes
(a) hexetidine and imidazolidinyl urea and
(b) at least one oxidation dye precursor and/or one direct dye.

In an especially preferred embodiment, an agent according to the invention for coloring keratin fibers is characterized in that it includes
(a) hexetidine and hexamethylenetetramine and
(b) at least one oxidation dye precursor and/or one direct dye.

In an especially preferred embodiment, an agent according to the invention for coloring keratin fibers is characterized in that it includes
(a) hexetidine and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) hexetidine and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) hexetidine and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) hexetidine and bromochlorophene and
(b) at least one oxidation dye precursor and/or one direct dye.

In an especially preferred embodiment, an agent according to the invention for coloring keratin fibers is characterized in that it includes
(a) hexetidine and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) hexetidine and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) hexetidine and 2-benzyl-4-chlorophenol and
(b) at least one oxidation dye precursor and/or one direct dye.

In an especially preferred embodiment, an agent according to the invention for coloring keratin fibers is characterized in that it includes
(a) hexetidine and 2-chloroacetamide and
(b) at least one oxidation dye precursor and/or one direct dye.

In an especially preferred embodiment, an agent according to the invention for coloring keratin fibers is characterized in that it includes
(a) hexetidine and chlorohexidine and
(b) at least one oxidation dye precursor and/or one direct dye.

In an especially preferred embodiment, an agent according to the invention for coloring keratin fibers is characterized in that it includes
(a) hexetidine and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) hexetidine and 1-phenoxy-propane-2-ol and
(b) at least one oxidation dye precursor and/or one direct dye.

In an especially preferred embodiment, an agent according to the invention for coloring keratin fibers is characterized in that it includes
(a) hexetidine and hexamidine and
(b) at least one oxidation dye precursor and/or one direct dye.

In an especially preferred embodiment, an agent according to the invention for coloring keratin fibers is characterized in that it includes
(a) hexetidine and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) hexetidine and chlorphenesin and
(b) at least one oxidation dye precursor and/or one direct dye.

In an especially preferred embodiment, an agent according to the invention for coloring keratin fibers is characterized in that it includes
(a) hexetidine and sodium hydroxymethyl amino acetate and
(b) at least one oxidation dye precursor and/or one direct dye.

In an especially preferred embodiment, an agent according to the invention for coloring keratin fibers is characterized in that it includes
(a) hexetidine and benzyl hemiformal and
(b) at least one oxidation dye precursor and/or one direct dye.

In an especially preferred embodiment, an agent according to the invention for coloring keratin fibers is characterized in that it includes
(a) hexetidine and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) hexetidine and methylisothiazolinone and
(b) at least one oxidation dye precursor and/or one direct dye.

In an especially preferred embodiment, an agent according to the invention for coloring keratin fibers is characterized in that it includes
(a) hexetidine and ethyl lauroyl arginate and
(b) at least one oxidation dye precursor and/or one direct dye.

In an especially preferred embodiment, an agent according to the invention for coloring keratin fibers is characterized in that it includes
(a) trichlorocarban and triclosan and
(b) at least one oxidation dye precursor and/or one direct dye.

In an especially preferred embodiment, an agent according to the invention for coloring keratin fibers is characterized in that it includes
(a) trichlorocarban and 4-chloro-3,4-dimethylphenol and
(b) at least one oxidation dye precursor and/or one direct dye.

In an especially preferred embodiment, an agent according to the invention for coloring keratin fibers is characterized in that it includes
(a) trichlorocarban and imidazolidinyl urea and
(b) at least one oxidation dye precursor and/or one direct dye.

In an especially preferred embodiment, an agent according to the invention for coloring keratin fibers is characterized in that it includes
(a) trichlorocarban and hexamethylenetetramine and
(b) at least one oxidation dye precursor and/or one direct dye.

In an especially preferred embodiment, an agent according to the invention for coloring keratin fibers is characterized in that it includes
(a) trichlorocarban and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) trichlorocarban and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) trichlorocarban and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) trichlorocarban and bromochlorophene and
(b) at least one oxidation dye precursor and/or one direct dye.

In an especially preferred embodiment, an agent according to the invention for coloring keratin fibers is characterized in that it includes
(a) trichlorocarban and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) trichlorocarban and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) trichlorocarban and 2-benzyl-4-chlorophenol and
(b) at least one oxidation dye precursor and/or one direct dye.

In an especially preferred embodiment, an agent according to the invention for coloring keratin fibers is characterized in that it includes
(a) trichlorocarban and 2-chloroacetamide and
(b) at least one oxidation dye precursor and/or one direct dye.

In an especially preferred embodiment, an agent according to the invention for coloring keratin fibers is characterized in that it includes
(a) trichlorocarban and chlorohexidine and
(b) at least one oxidation dye precursor and/or one direct dye.

In an especially preferred embodiment, an agent according to the invention for coloring keratin fibers is characterized in that it includes
(a) trichlorocarban and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) trichlorocarban and 1-phenoxy-propane-2-ol, hexamidine and
(b) at least one oxidation dye precursor and/or one direct dye.

In an especially preferred embodiment, an agent according to the invention for coloring keratin fibers is characterized in that it includes
(a) trichlorocarban and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) trichlorocarban and chlorphenesin and
(b) at least one oxidation dye precursor and/or one direct dye.

In an especially preferred embodiment, an agent according to the invention for coloring keratin fibers is characterized in that it includes
(a) trichlorocarban and sodium hydroxymethyl amino acetate and
(b) at least one oxidation dye precursor and/or one direct dye.

In an especially preferred embodiment, an agent according to the invention for coloring keratin fibers is characterized in that it includes
(a) trichlorocarban and benzyl hemiformal and
(b) at least one oxidation dye precursor and/or one direct dye.

In an especially preferred embodiment, an agent according to the invention for coloring keratin fibers is characterized in that it includes
(a) trichlorocarban and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) trichlorocarban and methylisothiazolinone and
(b) at least one oxidation dye precursor and/or one direct dye.

In an especially preferred embodiment, an agent according to the invention for coloring keratin fibers is characterized in that it includes
(a) trichlorocarban and ethyl lauroyl arginate and
(b) at least one oxidation dye precursor and/or one direct dye.

In an especially preferred embodiment, an agent according to the invention for coloring keratin fibers is characterized in that it includes
(a) triclosan and 4-chloro-3,4-dimethylphenol and
(b) at least one oxidation dye precursor and/or one direct dye.

In an especially preferred embodiment, an agent according to the invention for coloring keratin fibers is characterized in that it includes
(a) triclosan and imidazolidinyl urea and
(b) at least one oxidation dye precursor and/or one direct dye.

In an especially preferred embodiment, an agent according to the invention for coloring keratin fibers is characterized in that it includes
(a) triclosan and hexamethylenetetramine and
(b) at least one oxidation dye precursor and/or one direct dye.

In an especially preferred embodiment, an agent according to the invention for coloring keratin fibers is characterized in that it includes
(a) triclosan and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes (a) triclosan and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) triclosan and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) triclosan and bromochlorophene and
(b) at least one oxidation dye precursor and/or one direct dye.

In an especially preferred embodiment, an agent according to the invention for coloring keratin fibers is characterized in that it includes
(a) triclosan and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) triclosan and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) triclosan and 2-benzyl-4-chlorophenol and
(b) at least one oxidation dye precursor and/or one direct dye.

In an especially preferred embodiment, an agent according to the invention for coloring keratin fibers is characterized in that it includes
(a) triclosan and 2-chloroacetamide and
(b) at least one oxidation dye precursor and/or one direct dye.

In an especially preferred embodiment, an agent according to the invention for coloring keratin fibers is characterized in that it includes
(a) triclosan and chlorohexidine and
(b) at least one oxidation dye precursor and/or one direct dye.

In an especially preferred embodiment, an agent according to the invention for coloring keratin fibers is characterized in that it includes
(a) triclosan and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) triclosan and 1-phenoxy-propane-2-ol, hexamidine and
(b) at least one oxidation dye precursor and/or one direct dye.

In an especially preferred embodiment, an agent according to the invention for coloring keratin fibers is characterized in that it includes
(a) triclosan and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) triclosan and chlorphenesin and
(b) at least one oxidation dye precursor and/or one direct dye.

In an especially preferred embodiment, an agent according to the invention for coloring keratin fibers is characterized in that it includes
(a) triclosan and sodium hydroxymethyl amino acetate and
(b) at least one oxidation dye precursor and/or one direct dye.

In an especially preferred embodiment, an agent according to the invention for coloring keratin fibers is characterized in that it includes
(a) triclosan and benzyl hemiformal and
(b) at least one oxidation dye precursor and/or one direct dye.

In an especially preferred embodiment, an agent according to the invention for coloring keratin fibers is characterized in that it includes
(a) triclosan and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) triclosan and methylisothiazolinone and
(b) at least one oxidation dye precursor and/or one direct dye.

In an especially preferred embodiment, an agent according to the invention for coloring keratin fibers is characterized in that it includes
(a) triclosan and ethyl lauroyl arginate and
(b) at least one oxidation dye precursor and/or one direct dye.

In an especially preferred embodiment, an agent according to the invention for coloring keratin fibers is characterized in that it includes
(a) 4-chloro-3,4-dimethylphenol and imidazolidinyl urea and
(b) at least one oxidation dye precursor and/or one direct dye.

In an especially preferred embodiment, an agent according to the invention for coloring keratin fibers is characterized in that it includes
(a) 4-chloro-3,4-dimethylphenol and hexamethylenetetramine and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes (a) 4-chloro-3,4-dimethylphenol and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) 4-chloro-3,4-dimethylphenol and bromochlorophene and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 2-benzyl-4-chlorophenol and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 2-chloroacetamide and
(b) at least one oxidation dye precursor and/or one direct dye.

In an especially preferred embodiment, an agent according to the invention for coloring keratin fibers is characterized in that it includes
(a) 4-chloro-3,4-dimethylphenol and chlorohexidine and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 1-phenoxy-propane-2-ol and
(b) at least one oxidation dye precursor and/or one direct dye.

In an especially preferred embodiment, an agent according to the invention for coloring keratin fibers is characterized in that it includes
(a) 4-chloro-3,4-dimethylphenol and hexamidine and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 4-chloro-3,4-dimethylphenol and chlorphenesin and
(b) at least one oxidation dye precursor and/or one direct dye.

In an especially preferred embodiment, an agent according to the invention for coloring keratin fibers is characterized in that it includes
(a) 4-chloro-3,4-dimethylphenol and sodium hydroxymethyl amino acetate and
(b) at least one oxidation dye precursor and/or one direct dye.

In an especially preferred embodiment, an agent according to the invention for coloring keratin fibers is characterized in that it includes
(a) 4-chloro-3,4-dimethylphenol and benzyl hemiformal and
(b) at least one oxidation dye precursor and/or one direct dye.

In an especially preferred embodiment, an agent according to the invention for coloring keratin fibers is characterized in that it includes
(a) 4-chloro-3,4-dimethylphenol and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 4-chloro-3,4-dimethylphenol and methylisothiazolinone and
(b) at least one oxidation dye precursor and/or one direct dye.

In an especially preferred embodiment, an agent according to the invention for coloring keratin fibers is characterized in that it includes
(a) 4-chloro-3,4-dimethylphenol and ethyl lauroyl arginate and
(b) at least one oxidation dye precursor and/or one direct dye.

In an especially preferred embodiment, an agent according to the invention for coloring keratin fibers is characterized in that it includes
(a) imidazolidinyl urea and hexamethylenetetramine and
(b) at least one oxidation dye precursor and/or one direct dye.

In an especially preferred embodiment, an agent according to the invention for coloring keratin fibers is characterized in that it includes
(a) imidazolidinyl urea and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) imidazolidinyl urea and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes (a) imidazolidinyl urea and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) imidazolidinyl urea and bromochlorophene and
(b) at least one oxidation dye precursor and/or one direct dye.

In an especially preferred embodiment, an agent according to the invention for coloring keratin fibers is characterized in that it includes
(a) imidazolidinyl urea and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) imidazolidinyl urea and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) imidazolidinyl urea and 2-benzyl-4-chlorophenol and
(b) at least one oxidation dye precursor and/or one direct dye.

In an especially preferred embodiment, an agent according to the invention for coloring keratin fibers is characterized in that it includes
(a) imidazolidinyl urea and 2-chloroacetamide and
(b) at least one oxidation dye precursor and/or one direct dye.

In an especially preferred embodiment, an agent according to the invention for coloring keratin fibers is characterized in that it includes
(a) imidazolidinyl urea and chlorohexidine and
(b) at least one oxidation dye precursor and/or one direct dye.

In an especially preferred embodiment, an agent according to the invention for coloring keratin fibers is characterized in that it includes
(a) imidazolidinyl urea and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) imidazolidinyl urea and 1-phenoxy-propane-2-ol and
(b) at least one oxidation dye precursor and/or one direct dye.

In an especially preferred embodiment, an agent according to the invention for coloring keratin fibers is characterized in that it includes
(a) imidazolidinyl urea and hexamidine and
(b) at least one oxidation dye precursor and/or one direct dye.

In an especially preferred embodiment, an agent according to the invention for coloring keratin fibers is characterized in that it includes
(a) imidazolidinyl urea and 5-ethyl-1-aza-3,7-dioxabicyclo[3.3.0]-octane and
(b) at least one oxidation dye precursor and/or one direct dye.

In an especially preferred embodiment, an agent according to the invention for coloring keratin fibers is characterized in that it includes
(a) imidazolidinyl urea and chlorphenesin and
(b) at least one oxidation dye precursor and/or one direct dye.

In an especially preferred embodiment, an agent according to the invention for coloring keratin fibers is characterized in that it includes
(a) imidazolidinyl urea and sodium hydroxymethyl amino acetate and
(b) at least one oxidation dye precursor and/or one direct dye.

In an especially preferred embodiment, an agent according to the invention for coloring keratin fibers is characterized in that it includes
(a) imidazolidinyl urea and benzyl hemiformal and
(b) at least one oxidation dye precursor and/or one direct dye.

In an especially preferred embodiment, an agent according to the invention for coloring keratin fibers is characterized in that it includes
(a) imidazolidinyl urea and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) imidazolidinyl urea and methylisothiazolinone and
(b) at least one oxidation dye precursor and/or one direct dye.

In an especially preferred embodiment, an agent according to the invention for coloring keratin fibers is characterized in that it includes
(a) imidazolidinyl urea and ethyl lauroyl arginate and
(b) at least one oxidation dye precursor and/or one direct dye.

In an especially preferred embodiment, an agent according to the invention for coloring keratin fibers is characterized in that it includes
(a) hexamethylenetetramine and 1-(4-chlorophenoxy)-1-(imidazole-1-yl)-3,3-dimethyl-2-butanone and
(b) at least one oxidation dye precursor and/or one direct dye.

In an especially preferred embodiment, an agent according to the invention for coloring keratin fibers is characterized in that it includes
(a) hexamethylenetetramine and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) hexamethylenetetramine and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) hexamethylenetetramine and bromochlorophene and
(b) at least one oxidation dye precursor and/or one direct dye.

In an especially preferred embodiment, an agent according to the invention for coloring keratin fibers is characterized in that it includes
(a) hexamethylenetetramine and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) hexamethylenetetramine and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) hexamethylenetetramine and 2-benzyl-4-chlorophenol and
(b) at least one oxidation dye precursor and/or one direct dye.

In an especially preferred embodiment, an agent according to the invention for coloring keratin fibers is characterized in that it includes
(a) hexamethylenetetramine and 2-chloroacetamide and
(b) at least one oxidation dye precursor and/or one direct dye.

In an especially preferred embodiment, an agent according to the invention for coloring keratin fibers is characterized in that it includes
(a) hexamethylenetetramine and chlorohexidine and
(b) at least one oxidation dye precursor and/or one direct dye.

In an especially preferred embodiment, an agent according to the invention for coloring keratin fibers is characterized in that it includes
(a) hexamethylenetetramine and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) hexamethylenetetramine and 1-phenoxy-propane-2-ol and
(b) at least one oxidation dye precursor and/or one direct dye.

In an especially preferred embodiment, an agent according to the invention for coloring keratin fibers is characterized in that it includes
(a) hexamethylenetetramine and hexamidine and
(b) at least one oxidation dye precursor and/or one direct dye.

In an especially preferred embodiment, an agent according to the invention for coloring keratin fibers is characterized in that it includes
(a) hexamethylenetetramine and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) hexamethylenetetramine and chlorphenesin and
(b) at least one oxidation dye precursor and/or one direct dye.

In an especially preferred embodiment, an agent according to the invention for coloring keratin fibers is characterized in that it includes
(a) hexamethylenetetramine and sodium hydroxymethyl amino acetate and
(b) at least one oxidation dye precursor and/or one direct dye.

In an especially preferred embodiment, an agent according to the invention for coloring keratin fibers is characterized in that it includes
(a) hexamethylenetetramine and benzyl hemiformal and
(b) at least one oxidation dye precursor and/or one direct dye.

In an especially preferred embodiment, an agent according to the invention for coloring keratin fibers is characterized in that it includes
(a) hexamethylenetetramine and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) hexamethylenetetramine and methylisothiazolinone and
(b) at least one oxidation dye precursor and/or one direct dye.

In an especially preferred embodiment, an agent according to the invention for coloring keratin fibers is characterized in that it includes
(a) hexamethylenetetramine and ethyl lauroyl arginate and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 1,3-bis-(hydroxymethyl)-5,5-dimethyl-2,4-imidazolidinedione and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and bromochlorophene and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 3-methyl-4-(1-methylethyl)phenol and (b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 2-benzyl-4-chlorophenol and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 2-chloroacetamide and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and chlorohexidine and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 1-phenoxy-propane-2-ol and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and hexamidine and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and chlorophenesin and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and sodium hydroxymethyl amino acetate and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and benzyl hemiformal and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and methylisothiazolinone and
(b) at least one oxidation dye precursor and/or one direct dye.

In an especially preferred embodiment, an agent according to the invention for coloring keratin fibers is characterized in that it includes
(a) 1-(4-chlorophenoxy)-1-(imidazole-1-yl)-3,3-dimethyl-2-butanone and ethyl lauroyl arginate and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 1-hydroxy-4-methyl-6-(2,4,4-trimethylpentyl)-2-pyridone and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and bromochlorophene and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes (a) 1,3-bis-(hydroxymethyl)-5,5-dimethyl-2,4-imidazolidinedione and 2-benzyl-4-chlorophenol and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 2-chloroacetamide and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and chlorohexidine and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 1-phenoxy-propane-2-ol and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and hexamidine and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and chlorophenesin and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and sodium hydroxymethyl amino acetate and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and benzyl hemiformal and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and 3-iodo-2-propinyl-butylcarbamate and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and methylisothiazolinone and
(b) at least one oxidation dye precursor and/or one direct dye.

In an especially preferred embodiment, an agent according to the invention for coloring keratin fibers is characterized in that it includes
(a) 1,3-bis-(hydroxymethyl)-5,5-dimethyl-2,4-imidazolidinedione and ethyl lauroyl arginate and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and bromochlorophene and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 2-benzyl-4-chlorophenol and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 2-chloroacetamide and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and chlorohexidine and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 1-phenoxy-propane-2-ol and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and hexamidine and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and chlorophenesin and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and sodium hydroxymethyl amino acetate and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and benzyl hemiformal and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and methylisothiazolinone and
(b) at least one oxidation dye precursor and/or one direct dye.

In an especially preferred embodiment, an agent according to the invention for coloring keratin fibers is characterized in that it includes
(a) 1-hydroxy-4-methyl-6-(2,4,4-trimethylpentyl)-2-pyridone and ethyl lauroyl arginate and
(b) at least one oxidation dye precursor and/or one direct dye.

In an especially preferred embodiment, an agent according to the invention for coloring keratin fibers is characterized in that it includes
(a) bromochlorophene and 3-methyl-4-(1-methylethyl)phenol and
(b) at least one oxidation dye precursor and/or one direct dye.

In an especially preferred embodiment, an agent according to the invention for coloring keratin fibers is characterized in that it includes
(a) bromochlorophene and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) bromochlorophene and 2-benzyl-4-chlorophenol and
(b) at least one oxidation dye precursor and/or one direct dye.

In an especially preferred embodiment, an agent according to the invention for coloring keratin fibers is characterized in that it includes
(a) bromochlorophene and 2-chloroacetamide and
(b) at least one oxidation dye precursor and/or one direct dye.

In an especially preferred embodiment, an agent according to the invention for coloring keratin fibers is characterized in that it includes
(a) bromochlorophene and chlorohexidine and
(b) at least one oxidation dye precursor and/or one direct dye.

In an especially preferred embodiment, an agent according to the invention for coloring keratin fibers is characterized in that it includes
(a) bromochlorophene and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) bromochlorophene and 1-phenoxy-propane-2-ol and
(b) at least one oxidation dye precursor and/or one direct dye.

In an especially preferred embodiment, an agent according to the invention for coloring keratin fibers is characterized in that it includes
(a) bromochlorophene and hexamidine and
(b) at least one oxidation dye precursor and/or one direct dye.

In an especially preferred embodiment, an agent according to the invention for coloring keratin fibers is characterized in that it includes
(a) bromochlorophene and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) bromochlorophene and chlorophenesin and
(b) at least one oxidation dye precursor and/or one direct dye.

In an especially preferred embodiment, an agent according to the invention for coloring keratin fibers is characterized in that it includes
(a) bromochlorophene and sodium hydroxymethyl amino acetate and
(b) at least one oxidation dye precursor and/or one direct dye.

In an especially preferred embodiment, an agent according to the invention for coloring keratin fibers is characterized in that it includes
(a) bromochlorophene and benzyl hemiformal and
(b) at least one oxidation dye precursor and/or one direct dye.

In an especially preferred embodiment, an agent according to the invention for coloring keratin fibers is characterized in that it includes
(a) bromochlorophene and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) bromochlorophene and methylisothiazolinone and
(b) at least one oxidation dye precursor and/or one direct dye.

In an especially preferred embodiment, an agent according to the invention for coloring keratin fibers is characterized in that it includes
(a) bromochlorophene and ethyl lauroyl arginate and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 5-chloro-2-methyl-3(2H)-isothiazolone and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 2-benzyl-4-chlorophenol and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 2-chloroacetamide and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and chlorohexidine and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 1-phenoxy-propane-2-ol and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and hexamidine and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and chlorophenesin and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and sodium hydroxymethyl amino acetate and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and benzyl hemiformal and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and methylisothiazolinone and
(b) at least one oxidation dye precursor and/or one direct dye.

In an especially preferred embodiment, an agent according to the invention for coloring keratin fibers is characterized in that it includes
(a) 3-methyl-4-(1-methylethyl)phenol and ethyl lauroyl arginate and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and 2-benzyl-4-chlorophenol and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and 2-chloroacetamide and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and chlorohexidine and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and 1-phenoxy-propane-2-ol and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and hexamidine and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and chlorophenesin and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and sodium hydroxymethyl amino acetate and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and benzyl hemiformal and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and methylisothiazolinone and
(b) at least one oxidation dye precursor and/or one direct dye.

In an especially preferred embodiment, an agent according to the invention for coloring keratin fibers is characterized in that it includes
(a) 5-chloro-2-methyl-3(2H)-isothiazolone and ethyl lauroyl arginate and
(b) at least one oxidation dye precursor and/or one direct dye.

In an especially preferred embodiment, an agent according to the invention for coloring keratin fibers is characterized in that it includes
(a) 2-benzyl-4-chlorophenol and 2-chloroacetamide and
(b) at least one oxidation dye precursor and/or one direct dye.

In an especially preferred embodiment, an agent according to the invention for coloring keratin fibers is characterized in that it includes
(a) 2-benzyl-4-chlorophenol and chlorohexidine and
(b) at least one oxidation dye precursor and/or one direct dye.

In an especially preferred embodiment, an agent according to the invention for coloring keratin fibers is characterized in that it includes
(a) 2-benzyl-4-chlorophenol and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 2-benzyl-4-chlorophenol and 1-phenoxy-propane-2-ol and
(b) at least one oxidation dye precursor and/or one direct dye.

In an especially preferred embodiment, an agent according to the invention for coloring keratin fibers is characterized in that it includes
(a) 2-benzyl-4-chlorophenol and hexamidine and
(b) at least one oxidation dye precursor and/or one direct dye.

In an especially preferred embodiment, an agent according to the invention for coloring keratin fibers is characterized in that it includes (a) 2-benzyl-4-chlorophenol and 5-ethyl-1-aza-3,7-dioxabi-cyclo-[3.3.0]-octane and
(b) at least one oxidation dye precursor and/or one direct dye.

In an especially preferred embodiment, an agent according to the invention for coloring keratin fibers is characterized in that it includes
(a) 2-benzyl-4-chlorophenol and chlorophenesin and
(b) at least one oxidation dye precursor and/or one direct dye.

In an especially preferred embodiment, an agent according to the invention for coloring keratin fibers is characterized in that it includes
(a) 2-benzyl-4-chlorophenol and sodium hydroxymethyl amino acetate and
(b) at least one oxidation dye precursor and/or one direct dye.

In an especially preferred embodiment, an agent according to the invention for coloring keratin fibers is characterized in that it includes
(a) 2-benzyl-4-chlorophenol and benzyl hemiformal and
(b) at least one oxidation dye precursor and/or one direct dye.

In an especially preferred embodiment, an agent according to the invention for coloring keratin fibers is characterized in that it includes
(a) 2-benzyl-4-chlorophenol and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 2-benzyl-4-chlorophenol and methylisothiazolinone and
(b) at least one oxidation dye precursor and/or one direct dye.

In an especially preferred embodiment, an agent according to the invention for coloring keratin fibers is characterized in that it includes
(a) 2-benzyl-4-chlorophenol and ethyl lauroyl arginate and
(b) at least one oxidation dye precursor and/or one direct dye.

In an especially preferred embodiment, an agent according to the invention for coloring keratin fibers is characterized in that it includes
(a) 2-chloroacetamide and chlorhexidine and
(b) at least one oxidation dye precursor and/or one direct dye.

In an especially preferred embodiment, an agent according to the invention for coloring keratin fibers is characterized in that it includes
(a) 2-chloroacetamide and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 2-chloroacetamide acid and 1-phenoxy-propane-2-ol and
(b) at least one oxidation dye precursor and/or one direct dye.

In an especially preferred embodiment, an agent according to the invention for coloring keratin fibers is characterized in that it includes
(a) 2-chloroacetamide and hexamidine and
(b) at least one oxidation dye precursor and/or one direct dye.

In an especially preferred embodiment, an agent according to the invention for coloring keratin fibers is characterized in that it includes
(a) 2-chloroacetamide and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 2-chloroacetamide and chlorophenesin and
(b) at least one oxidation dye precursor and/or one direct dye.

In an especially preferred embodiment, an agent according to the invention for coloring keratin fibers is characterized in that it includes
(a) 2-chloroacetamide and sodium hydroxymethyl amino acetate and
(b) at least one oxidation dye precursor and/or one direct dye.

In an especially preferred embodiment, an agent according to the invention for coloring keratin fibers is characterized in that it includes
(a) 2-chloroacetamide and benzyl hemiformal and
(b) at least one oxidation dye precursor and/or one direct dye.

In an especially preferred embodiment, an agent according to the invention for coloring keratin fibers is characterized in that it includes
(a) 2-chloroacetamide and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 2-chloroacetamide and methylisothiazolinone and
(b) at least one oxidation dye precursor and/or one direct dye.

In an especially preferred embodiment, an agent according to the invention for coloring keratin fibers is characterized in that it includes
(a) 2-chloroacetamide and ethyl lauroyl arginate and
(b) at least one oxidation dye precursor and/or one direct dye.

In an especially preferred embodiment, an agent according to the invention for coloring keratin fibers is characterized in that it includes
(a) chlorohexidine and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) chlorohexidine and 1-phenoxy-propane-2-ol and
(b) at least one oxidation dye precursor and/or one direct dye.

In an especially preferred embodiment, an agent according to the invention for coloring keratin fibers is characterized in that it includes
(a) chlorohexidine and hexamidine and
(b) at least one oxidation dye precursor and/or one direct dye.

In an especially preferred embodiment, an agent according to the invention for coloring keratin fibers is characterized in that it includes (a) chlorohexidine and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) chlorohexidine and chlorophenesin and
(b) at least one oxidation dye precursor and/or one direct dye.

In an especially preferred embodiment, an agent according to the invention for coloring keratin fibers is characterized in that it includes
(a) chlorohexidine and sodium hydroxymethyl amino acetate and
(b) at least one oxidation dye precursor and/or one direct dye.

In an especially preferred embodiment, an agent according to the invention for coloring keratin fibers is characterized in that it includes
(a) chlorohexidine and benzyl hemiformal and
(b) at least one oxidation dye precursor and/or one direct dye.

In an especially preferred embodiment, an agent according to the invention for coloring keratin fibers is characterized in that it includes
(a) chlorohexidine and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) chlorohexidine and methylisothiazolinone and
(b) at least one oxidation dye precursor and/or one direct dye.

In an especially preferred embodiment, an agent according to the invention for coloring keratin fibers is characterized in that it includes
(a) chlorohexidine and ethyl lauroyl arginate and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and 1-phenoxy-propane-2-ol and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and 4,4-dimethyl-1,3-oxazolidine and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and chlorophenesin and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and sodium hydroxymethyl amino acetate and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and benzyl hemiformal and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and methylisothiazolinone and
(b) at least one oxidation dye precursor and/or one direct dye.

In an especially preferred embodiment, an agent according to the invention for coloring keratin fibers is characterized in that it includes
(a) 4,4-dimethyl-1,3-oxazolidine and ethyl lauroyl arginate and
(b) at least one oxidation dye precursor and/or one direct dye.

In an especially preferred embodiment, an agent according to the invention for coloring keratin fibers is characterized in that it includes
(a) 1-phenoxy-propane-2-ol and hexamidine and
(b) at least one oxidation dye precursor and/or one direct dye.

In an especially preferred embodiment, an agent according to the invention for coloring keratin fibers is characterized in that it includes
(a) 1-phenoxy-propane-2-ol and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) 1-phenoxy-propane-2-ol and chlorophenesin and
(b) at least one oxidation dye precursor and/or one direct dye.

In an especially preferred embodiment, an agent according to the invention for coloring keratin fibers is characterized in that it includes
(a) 1-phenoxy-propane-2-ol and sodium hydroxymethyl amino acetate and
(b) at least one oxidation dye precursor and/or one direct dye.

In an especially preferred embodiment, an agent according to the invention for coloring keratin fibers is characterized in that it includes
(a) 1-phenoxy-propane-2-ol and benzyl hemiformal and
(b) at least one oxidation dye precursor and/or one direct dye.

In an especially preferred embodiment, an agent according to the invention for coloring keratin fibers is characterized in that it includes
(a) 1-phenoxy-propane-2-ol and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 1-phenoxy-propane-2-ol and methylisothiazolinone and
(b) at least one oxidation dye precursor and/or one direct dye.

In an especially preferred embodiment, an agent according to the invention for coloring keratin fibers is characterized in that it includes
(a) 1-phenoxy-propane-2-ol and ethyl lauroyl arginate and
(b) at least one oxidation dye precursor and/or one direct dye.

In an especially preferred embodiment, an agent according to the invention for coloring keratin fibers is characterized in that it includes
(a) hexamidine and 5-ethyl-1-aza-3,7-dioxabicyclo-[3.3.0]-octane and
(b) at least one oxidation dye precursor and/or one direct dye.

In an especially preferred embodiment, an agent according to the invention for coloring keratin fibers is characterized in that it includes
(a) hexamidine and chlorphenesin and
(b) at least one oxidation dye precursor and/or one direct dye.

In an especially preferred embodiment, an agent according to the invention for coloring keratin fibers is characterized in that it includes
(a) hexamidine and sodium hydroxymethyl amino acetate and
(b) at least one oxidation dye precursor and/or one direct dye.

In an especially preferred embodiment, an agent according to the invention for coloring keratin fibers is characterized in that it includes
(a) hexamidine and benzyl hemiformal and
(b) at least one oxidation dye precursor and/or one direct dye.

In an especially preferred embodiment, an agent according to the invention for coloring keratin fibers is characterized in that it includes
(a) hexamidine and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) hexamidine and methylisothiazolinone and
(b) at least one oxidation dye precursor and/or one direct dye.

In an especially preferred embodiment, an agent according to the invention for coloring keratin fibers is characterized in that it includes
(a) hexamidine and ethyl lauroyl arginate and
(b) at least one oxidation dye precursor and/or one direct dye.

In an especially preferred embodiment, an agent according to the invention for coloring keratin fibers is characterized in that it includes
(a) 5-ethyl-1-aza-3,7-dioxabicyclo-[3.3.0]-octane and chlorophenesin and
(b) at least one oxidation dye precursor and/or one direct dye.

In an especially preferred embodiment, an agent according to the invention for coloring keratin fibers is characterized in that it includes
(a) 5-ethyl-1-aza-3,7-dioxabicyclo-[3.3.0]-octane and sodium hydroxymethyl amino acetate and
(b) at least one oxidation dye precursor and/or one direct dye.

In an especially preferred embodiment, an agent according to the invention for coloring keratin fibers is characterized in that it includes
(a) 5-ethyl-1-aza-3,7-dioxabicyclo-[3.3.0]-octane and benzyl hemiformal and
(b) at least one oxidation dye precursor and/or one direct dye.

In an especially preferred embodiment, an agent according to the invention for coloring keratin fibers is characterized in that it includes
(a) 5-ethyl-1-aza-3,7-dioxabicyclo-[3.3.0]-octane and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) 5-ethyl-1-aza-3,7-dioxabicyclo-[3.3.0]-octane and methylisothiazolinone and
(b) at least one oxidation dye precursor and/or one direct dye.

In an especially preferred embodiment, an agent according to the invention for coloring keratin fibers is characterized in that it includes
(a) 5-ethyl-1-aza-3,7-dioxabicyclo-[3.3.0]-octane and ethyl lauroyl arginate and
(b) at least one oxidation dye precursor and/or one direct dye.

In an especially preferred embodiment, an agent according to the invention for coloring keratin fibers is characterized in that it includes
(a) chlorophenesin and sodium hydroxymethyl amino acetate and
(b) at least one oxidation dye precursor and/or one direct dye.

In an especially preferred embodiment, an agent according to the invention for coloring keratin fibers is characterized in that it includes
(a) chlorophenesin and benzyl hemiformal and
(b) at least one oxidation dye precursor and/or one direct dye.

In an especially preferred embodiment, an agent according to the invention for coloring keratin fibers is characterized in that it includes
(a) chlorophenesin and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) chlorophenesin and methylisothiazolinone and
(b) at least one oxidation dye precursor and/or one direct dye.

In an especially preferred embodiment, an agent according to the invention for coloring keratin fibers is characterized in that it includes
(a) chlorophenesin and ethyl lauroyl arginate and
(b) at least one oxidation dye precursor and/or one direct dye.

In an especially preferred embodiment, an agent according to the invention for coloring keratin fibers is characterized in that it includes
(a) sodium hydroxymethyl amino acetate and benzyl hemiformal and
(b) at least one oxidation dye precursor and/or one direct dye.

In an especially preferred embodiment, an agent according to the invention for coloring keratin fibers is characterized in that it includes
(a) sodium hydroxymethyl amino acetate and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) sodium hydroxymethyl amino acetate and methylisothiazolinone and
(b) at least one oxidation dye precursor and/or one direct dye.

In an especially preferred embodiment, an agent according to the invention for coloring keratin fibers is characterized in that it includes
(a) sodium hydroxymethyl amino acetate and ethyl lauroyl arginate and
(b) at least one oxidation dye precursor and/or one direct dye.

In an especially preferred embodiment, an agent according to the invention for coloring keratin fibers is characterized in that it includes
(a) benzyl hemiformal and 3-iodo-2-propynyl butylcarbamate and
(b) at least one oxidation dye precursor and/or one direct dye.

In an especially preferred embodiment, an agent according to the invention for coloring keratin fibers is characterized in that it includes
(a) benzyl hemiformal and methylisothiazolinone and
(b) at least one oxidation dye precursor and/or one direct dye.

In an especially preferred embodiment, an agent according to the invention for coloring keratin fibers is characterized in that it includes
(a) benzyl hemiformal and ethyl lauroyl arginate and
(b) at least one oxidation dye precursor and/or one direct dye.

In an especially preferred embodiment, an agent according to the invention for coloring keratin fibers is characterized in that it includes
(a) 3-iodo-2-propynyl butylcarbamate and methylisothiazolinone and
(b) at least one oxidation dye precursor and/or one direct dye.

In an especially preferred embodiment, an agent according to the invention for coloring keratin fibers is characterized in that it includes
(a) 3-iodo-2-propynyl butylcarbamate and ethyl lauroyl arginate and
(b) at least one oxidation dye precursor and/or one direct dye.

In an especially preferred embodiment, an agent according to the invention for coloring keratin fibers is characterized in that it includes
(a) methylisothiazolinone and ethyl lauroyl arginate and
(b) at least one oxidation dye precursor and/or one direct dye.

A very good preservative effect was also able to be achieved if at least three of the preservatives from group (a) were used in agents according to the invention for coloring keratinic fibers. It was found that the use of at least three preservatives from group (a) improves the preservative effect in a synergistic manner.

In an especially preferred embodiment, an agent according to the invention for coloring keratinic fibers is characterized in that it includes
(a) at least three preservatives from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate.

Which preservatives are optimally used in what quantities depends, for one, on the legal requirements and, for another, on the effectiveness of the respective preservative. It is advantageous if the agent according to the invention includes the preservative or preservatives (a) in a total quantity from 0.001 to 5.0 wt %, preferably 0.01 to 2.0 wt %, more preferably 0.1 to 1.0 wt %, and very especially preferably 0.1 to 0.6 wt %. All of the quantities indicated here refer to the total weight of all of the preservatives from group (a) included in the agent in relation to the total weight of the agent.

In an especially preferred embodiment, an agent according to the invention for coloring keratin fibers is characterized in that it includes—with respect to the total weight of the agent—one or more preservatives (a) in a total quantity from 0.001 to 5.0 wt %, preferably 0.01 to 2.0 wt %, more preferably 0.1 to 1.0 wt % and very especially preferably 0.1 to 0.6 wt %.

Certain preservatives from group (a) have proven to be very especially suitable for use in colorants. It was especially advantageous to use at least one compound from group (a), which consists of 2-hydroxydiphenyl, dehydroacetic acid, dibromohexamidine, 10-undecylenic acid, hexetidine, triclocarban, triclosan, 4-imidazolidinyl urea, 1-(4-chlorophenoxy)-1-(imidazole-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 2-benzyl-4-chlorophenol, chlorohexidine, hexamidine, 5-ethyl-1-aza-3,7-dioxabicyclo-[3.3.0]-octane, chlorphenesin, 3-iodo-2-propynyl butylcarbamate, and ethyl lauroyl arginate.

In another especially preferred embodiment, an agent according to the invention for coloring keratinic fibers is characterized in that it includes
(a) at least one preservative from group of 2-hydroxydiphenyl, dehydroacetic acid, dibromohexamidine, 10-undecylenic acid, hexetidine, triclocarban, triclosan, 4-imidazolidinyl urea, 1-(4-chlorophenoxy)-1-(imidazole-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 2-benzyl-4-chlorophenol, chlorohexidine, hexamidine, 5-ethyl-1-aza-3,7-dioxabicyclo-[3.3.0]-octane, chlorphenesin, 3-iodo-2-propynyl butylcarbamate, and ethyl lauroyl arginate.

Moreover, the preservatives can also be combined especially well with a second group of preservatives (c). This second group of preservatives (c) is the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

Through the combination of preservatives from groups (a) and (c), an outstanding preservative effect was able to be achieved without disadvantageously affecting the colorations on the keratinic fibers in terms of their intensity, the desired color nuance and their fastness characteristics.

In another especially preferred embodiment, an agent according to the invention for coloring keratinic fibers is characterized in that it includes
(a) at least one preservative from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate, and
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) sorbic acid,
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 2-hydroxydiphenyl,
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 4-hydroxybenzoic acid,
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) dehydroacetic acid and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) dibromohexamidine and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 10-undecylenic acid and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) hexetidine and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) trichlorocarban and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) triclosan, and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 4-chloro-3,4-dimethylphenol, and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) imidazolidinyl urea and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) hexamethylenetetramine and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 1-(4-chlorophenoxy)-1-(imidazole-1-yl)-3,3-dimethyl-2-butanone, and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 1,3-bis-(hydroxymethyl)-5,5-dimethyl-2,4-imidazolidinedione and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 1-hydroxy-4-methyl-6-(2,4,4-trimethylpentyl)-2-pyridone and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 5-chloro-2-methyl-3(2H)-isothiazolone and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 2-benzyl-4-chlorophenol and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 2-chloroacetamide and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) chlorohexidine and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 4,4-dimethyl-1,3-oxazolidine and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 1-phenoxy-propane-2-ol and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) hexamidine and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 5-ethyl-1-aza-3,7-dioxabicyclo-[3.3.0]-octane and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) chlorophenesin and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) sodium hydroxymethyl amino acetate and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) benzyl hemiformal and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 3-iodo-2-propynyl butylcarbamate and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) 3-methylisothiazolinone and
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

In another especially preferred embodiment, an agent according to the invention for coloring keratin fibers is characterized in that it includes
(a) ethyl lauroyl arginate
(b) at least one direct dye,
(c) at least one preservative from the group consisting of sodium sulfite, sodium hydrogen sulfate, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol and ethanol.

Which preservatives from group (c) are optimally used in what quantities again depends, for one, on the legal requirements and, for another, on the effectiveness of the respective preservative. It is advantageous if the agent according to the invention includes the additional preservative or preservatives (c) in a total quantity from 0.001 to 5.0 wt %, preferably 0.01 to 2.0 wt %, more preferably 0.1 to 1.0 wt %, and very especially preferably 0.1 to 0.6 wt %. All of the quantities indicated here refer to the total weight of all of the preservatives from group (c) included in the agent in relation to the total weight of the agent.

In an especially preferred embodiment, an agent according to the invention for coloring keratin fibers is characterized in that it includes—with respect to the total weight of the agent—one or more preservatives (c) in a total quantity from 0.001 to 5.0 wt %, preferably 0.01 to 2.0 wt %, more preferably 0.1 to 1.0 wt % and very especially preferably 0.1 to 0.6 wt %.

The above-described preservatives from group (a) and the especially preferred combinations of preservatives from group (a) and from groups (a) and (c) can be used both for preserving colorants that include direct dyes and for preserving colorants that include oxidation dye precursors.

In another especially preferred embodiment, an agent according to the invention for coloring keratinic fibers is characterized in that it includes
(b) at least one direct dye.

Direct dyes can be categorized into anionic, cationic and nonionic direct dyes. The direct dyes are preferably selected from the nitro-phenylenediamines, the nitro-aminophenols, the azo dyes, the anthraquinones, the triarylmethane dyes or the indophenols and the physiologically acceptable salts thereof. The additional direct dyes are each preferable used in a proportion from 0.001 to 2 wt % with respect to the entire applied preparation.

In another especially preferred embodiment, an agent according to the invention for coloring keratinic fibers is characterized in that it includes at least one neutral direct dye.

Nonionic nitro- and quinone dyes and neutral azo dyes merit special consideration as nonionic direct dyes. Preferred nonionic direct dyes are those known under the international designations and/or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)-amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chloro-2-nitrobenzol, 4-Amino-3-nitrophenol, 1-(2'-ureidoethyl)amino-4-nitrobenzol, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

In another especially preferred embodiment, an agent according to the invention for coloring keratinic fibers is characterized in that it includes at least one cationic direct dye as a direct dye.

Preferred cationic direct dyes are cationic triphenylmethane dyes such as, for example, Basic Blue 7, Basic Blue 26, Basic Violet 2 and Basic Violet 14, aromatic systems that are substituted with a quaternary nitrogen group, such as, for example, Basic Yellow 57, Basic Red 76, Basic Blue 99, Basic Brown 16 and Basic Brown 17, cationic anthraquinone dyes such as HC Blue 16 (Bluequat B), as well as direct dyes including a heterocycle that has at least one quaternary nitrogen atom, particularly Basic Yellow 87, Basic Orange 31 and Basic Red 51. The cationic direct dyes that are sold under the trademark Arianor are also preferred cationic direct dyes according to the invention.

In another especially preferred embodiment, an agent according to the invention for coloring keratinic fibers is characterized in that it includes at least one anionic acid dye as a direct dye.

Preferred anionic direct dyes are the compounds known by the international designations and/or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol Blue and Tetrabromophenol Blue.

It is particularly preferred if the compound(s) of formula (I) are used in combination with Basic Yellow 57, Basic Red 76, Basic Brown 16 and Basic Brown 17 such as HC Blue 16 (Bluequat B), Basic Yellow 87, Basic Orange 31, Basic Red 51, HC Red 1, HC Red 3, HC Red 7, HC Red 10, HC Red 11, HC Red 13, HC Red BN, HC Blue 2, HC Blue 11, HC Blue 12, 2-amino-4-nitrophenol, 1,4-bis-(2-hydroxyethyl)-amino-2-nitrobenzol, 3-nitro-4-(2-hydroxyethyl)aminophenol, 4-[(2-hydroxyethyl)amino]-3-nitro-1-methylbenzol, 1-amino-4-(2-hydroxyethyl)amino-5-chloro-2-nitrobenzol, 4-amino-3-nitrophenol, 4-[(3-hydroxypropyl)amino]-3-nitrophenol and/or 4-nitro-o-phenylenediamine.

The direct dye(s) can be included in the agents according to the invention in a total quantity—with respect to the total weight of the agent—from 0.0001 to 5.0 wt %, preferably from 0.01 to 2.5 wt %, more preferably from 0.05 to 1.0 wt % and very especially preferably from 0.1 to 0.9 wt %.

As already described above, the preservatives from group (a) and the especially preferred combinations of preservatives from group (a) and from groups (a) and (c) can also be used very advantageously for preserving colorants that include oxidation dye precursors.

In another especially preferred embodiment, an agent according to the invention for coloring keratinic fibers is characterized in that it includes
(b) at least one oxidation dye precursor.

Developer components or developers in combination with coupler components or couplers are usually used as oxidation dye precursors. Under the influence of hydrogen peroxide, developers and couplers react with one another and, through oxidative coupling, form the actual dyes.

Suitable developer components are selected from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-Amino-3-methylphenyl)-N-[3-(1H-imidazole-1-yl)propyl]amine, N,N'-bis-(2-hydroxyethyl)-N,N'-bis-(4-aminophenyl)-1,3-diamino-propane-2-ol, bis-(2-hydroxy-5-aminophenyl)methane, 1,3-Bis-(2,5-diaminophenoxy)-propane-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, as well as the physiologically acceptable salts of these compounds. Especially preferred additional developer components are p-toluylenediamine, 2-(2-hydroxyethyl)-p-phenylenediamine, 2-methoxymethyl-p-phenylenediamine, N-(4-amino-3-methylphenyl)-N-[3-(1H- imidazole-1-yl)propyl]amine and/or 4,5-diamino-1-(2-hydroxyethyl)-pyrazole as well as the physiologically acceptable salts thereof.

Suitable coupler components can be selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-Bis(2'-hydroxyethyl amino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholine-4-yl(phenyl)amino]ethanol, 3-amino-4-(2-methoxyethoxy)-5-methylphenylamine, 1-amino-3-bis(2-hydroxyethyl)aminobenzene, resorcin, 2-methylresorcin, 4-chlororesorcin, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazole-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindol, 6-hydroxyindol, 7-hydroxyindol, 4-hydroxyindoline, 6-hydroxyindoline and/or 7-hydroxyindoline and physiologically acceptable salts thereof.

The developer(s) can be included in the agents according to the invention in a total quantity—with respect to the total weight of the agent—from 0.0001 to 5.0 wt %, preferably from 0.01 to 2.5 wt %, more preferably from 0.05 to 1.0 wt % and very especially preferably from 0.1 to 0.9 wt %.

The coupler(s) can be included in the agents according to the invention in a total quantity—with respect to the total weight of the agent—from 0.0001 to 5.0 wt %, preferably from 0.01 to 2.5 wt %, more preferably from 0.05 to 1.0 wt % and very especially preferably from 0.1 to 0.9 wt %.

Furthermore, the agents according to the invention can include other active substances, adjuvants and additives such as, for example, nonionic, anionic, cationic, zwitterionic or amphoteric surfactants and emulsifiers, fats, such as fatty alcohols, fatty acid esters or hydrocarbons, nonionic, cationic or anionic polymers, other thickeners, structurants such as glucose, maleic acid and lactic acid, hair-conditioning compounds, perfume oils, dimethyl isosorbide and cyclodextrins, solvents and solubilizers, fiber structure-improving active substances, particularly mono-, di- and oligosaccharides such as, for example, glucose, galactose, fructose, fruit sugar and lactose, quaternized amines such as methyl-1-alkylamidoethyl-2-alkylimidazolinium-methosulfate, defoamers such as silicones, dyes for coloring the agent, amino acids and oligopeptides, particularly arginine and/or serine, animal- and/or plant-based protein hydrolysates such as, for example, elastin, collagen, keratin, silk and milk protein hydrolysates, or almond, rice, pea, potato and wheat protein hydrolysates, as well as in the form of their fatty acid condensation products or, optionally, anionically or cationically modified derivatives, plant oils, for example macadamia nut oil, kukui nut oil, palm oil, amaranth seed oil, peach kernel oil, avocado oil, olive oil, coconut oil, rapeseed oil, sesame oil, jojoba oil, soy oil, peanut oil, evening primrose oil and tea tree oil, light stabilizers, particularly derivatized benzophenone, cinnamic acid derivatives and triazines, substances for setting the pH value such as, for example, common acids, particularly food-grade acids and bases, active substances such as panthenol, pantothenic acid, pantolactone, allantoin, pyrrolidinone carboxylic acids and salts thereof as well as bisabolol, polyphenols, plant extracts, cholesterol, bodying agents such as sugar esters, polyesters or polyolalkyl ether, waxes such as spermaceti, beeswax, montan wax and paraffins, fatty acid alkanolamides, swelling and penetration agents such as glycerin, propylene glycol monoethyl ether, carbonates, hydrogen carbonates, guanidine, ureas as well as primary, secondary and tertiary phosphates, opacifiers such as latex, styrene/PVP and styrene/acrylamide copolymers, pearlescent agents such as ethylene glycol mono- and distearate as well as PEG-3 distearate, pigments, stabilizers for hydrogen peroxide and other oxidizing agents, propellants such as propane/butane mixtures, $N_2O$, dimethyl ether, $CO_2$ and air, antioxidants.

The selection of these other substances is made by a person skilled in the art depending on the desired characteristics of the agents.

With respect to other optional components and the quantities used of these components, express reference is made to the relevant handbooks known to a person skilled in the art, such as Kh. Schrader, *Grundlagen und Rezepturen der Kosmetika* [Fundamentals and Formulations of Cosmetics], 2nd edition, Hüthig Buch Verlag, Heidelberg, 1989.

The previously described preservatives from group (a) and the combinations of preservative from group (a) as well as from groups (a) and (c) have outstanding suitability for the preservation of colorants.

Some of the preservatives (a) are reactive substances (e.g., formaldehyde splitters and the like) that can react with the dyes (b). Such reactions can result in undesired color shifting if the reaction between preservative and dye structurally modifies the dye and thus changes its chromophoric system.

Over the course of the work leading to this invention, it was found that the temperature at which the colorant is produced has an influence on the extent of the interaction between dye and preservative. It appears that particularly the maximum temperature at which the preservative (a) and the dues (b) come into contact with one another has an influence on the reactions taking place between the two substance groups.

During the manufacture of colorants, a fat base—which can be a mixture of fatty alcohols ($C_8$-$C_{30}$ alkanols), for instance—is usually fused, for example at a temperature of about 70° C. to 90° C. The other ingredients of the colorant (surfactants, care ingredients, etc.) are worked into this fused fat base. Depending on their water solubility, the preservatives (a) and the dyes (b) are either stirred directly into the fat base or first dissolved in water or water/solvent and then worked into the fat base. Water is then added to the fat base, and it is homogenized through stirring and set to the desired pH through the addition of acids/alkalizing agents.

It was found that undesired interactions between dyes (b) and preservatives (a) can be reduced if both the preservatives (a) according to the invention and the dyes (b) are worked into the fat base at a temperature of no more than 60° C. The especially preferred temperature range is 30° C.-50° C. Within this temperature range, the complete dissolution and homogenization of the ingredients in the base can be ensured without bringing about a significant reaction between preservative (a) and dye (b).

A second object of the present invention is therefore a method for manufacturing an agent for coloring keratinic fibers comprising the following steps:

(I) provision of a base formulation through heating of one or more fatty alcohols ($C_8$-$C_{30}$ alkanols) to a temperature of 70 to 90° C., (II) addition of one or more preservatives (a) as disclosed in detail in the description of the first object of the invention to the base formulation when the latter has a temperature of 30 to 60° C., (III) addition of one or more oxidation dye precursors and/or direct dyes (b) as disclosed in detail in the description of the first object of the invention to the base formulation when the latter has a temperature of 30 to 60° C., (IV) addition of water.

The liquefied base formulation is first brought to a temperature of 70 to 90° C. through the fusion of one or more $C_8$-$C_{30}$ fatty alcohols. Together with the $C_8$-$C_{30}$ fatty alcohols, additional fats or other basic materials can be included in the base formulation, with the additional fats or other basic materials being either fused together with the fatty alcohols or added to the base formulation after the fusion of the fatty alcohols. When the fatty alcohols (and, optionally, the other basic materials) have fused, the heat supply is reduced or halted, whereby the base formulation begins to slowly cool. Preferably, the base formulation is stirred during this process.

Once the cooling base formulation has then reached a temperature of 30 to 60° C., the preservative or the preservatives (a) are added to the base formulation, preferably also under stirring. This addition preferably occurs once the base formulation has reached a temperature of 30 to 50° C.

Once the cooling base formulation has then reached a temperature of 30 to 60° C., the dye or dyes (b) are also added to the base formulation, preferably also under stirring, either in substance or predissolved form. The addition preferably occurs once the base formulation has reached a temperature of 30 to 50° C.

Water is also added to the base formulation, and this mixture is homogenized, thus resulting in the finished emulsion.

Especially preferably, one or more surfactants/emulsifiers are also added to the colorant.

A method is preferred which is characterized by the (II) addition of one or more preservatives (a) as disclosed in detail in the description of the first object of the invention to the base formulation when the latter has a temperature of 30 to 50° C., and (III) addition of one or more oxidation dye precursors and/or direct dyes (b) as disclosed in detail in the description of the first object of the invention to the base formulation when the latter has a temperature of 30 to 50° C.

A method is preferred which comprises the following steps in the indicated sequence step (I) followed by step (II) followed by step (III) followed by step (IV).

A method is preferred which comprises the following steps in the indicated sequence step (I) followed by step (II) followed by step (IV) followed by step (III).

A method is preferred which comprises the following steps in the indicated sequence step (I) followed by step (III) followed by step (II) followed by step (IV).

A method is preferred which comprises the following steps in the indicated sequence step (I) followed by step (IV) followed by step (II) followed by step (III).

A method is preferred which comprises the following steps in the indicated sequence step (I) followed by step (IV) followed by step (III) followed by step (II).

A method for manufacturing an agent for coloring keratinic fibers is also especially preferred which comprises the following steps:

(I) provision of a base formulation through heating of one or more fatty alcohols ($C_8$-$C_{30}$ alkanols) to a temperature of 70 to 90° C., (II) addition of one or more preservatives (a) from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloro acetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate to the base formulation when the latter has a temperature of 30 to 60° C., (III) addition of one or more direct dyes (b) to the base formulation when the latter has a temperature of 30 to 60° C., (IV) addition of water.

A method for manufacturing an agent for coloring keratinic fibers is also especially preferred which comprises the following steps:

(I) provision of a base formulation through heating of one or more fatty alcohols ($C_8$-$C_{30}$ alkanols) to a temperature of 70 to 90° C., (II) addition of one or more preservatives (a) from the group of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloro acetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone and ethyl lauroyl arginate to the base formulation when the latter has a temperature of 30 to 60° C., (III) addition of one or more oxidation dye precursors (b) to the base formulation when the latter has a temperature of 30 to 60° C., (IV) addition of water.

As regards other preferred embodiments of the method according to the invention, the remarks concerning the agents according to the invention apply mutatis mutandis.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for manufacturing an agent for coloring keratinic fibers, comprising:
   (I) providing a base formulation through heating of one or more $C_8$-$C_{30}$ fatty alcohols to a temperature of 70 to 90° C.,
   (II) adding one or more preservatives (a) to the base formulation when the latter has a temperature of 30 to 60° C., the one or more preservatives being selected from the group consisting of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone, and ethyl lauroyl arginate,
   (III) adding one or more oxidation dye precursors and/or direct dyes (b) to the base formulation when the latter has a temperature of 30 to 60° C., and
   (IV) adding water to the base formulation.

2. The method as set forth in claim 1, wherein steps (II) and (III) include
   adding the one or more preservatives (a) to the base formulation when the latter has a temperature of 30 to 50° C., and
   adding the one or more oxidation dye precursors and/or direct dyes (b) to the base formulation when the latter has a temperature of 30 to 50° C.

3. The method as set forth in claim 1, wherein the step (II) of adding the one or more preservatives to the base formulation comprises adding
   at least two preservatives selected from the group consisting of sorbic acid, 2-hydroxydiphenyl, 4-hydroxybenzoic acid, dehydro acetic acid, dibromohexamidine, 10-undecylenic acid, hexetidinum, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3 (2H)-isothiazolone, 2-benzyl-4-chlorophenol, 2-chloroacetamide, chlorohexidine, 4, 4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone, and ethyl lauroyl arginate.

4. The method as set forth in claim 1, wherein the step (II) of adding the one or more preservatives to the base formulation comprises adding
   at least three preservatives selected from the group consisting of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4,4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone, and ethyl lauroyl arginate.

5. The method as set forth in claim 1, wherein the one or more preservatives are added to the base formulation in a total quantity from 0.001 to 5.0 wt %.

6. The method as set forth in claim 1, wherein the step (II) of adding the one or more preservatives to the base formulation comprises adding
   at least one preservative selected from group consisting of 2-hydroxydiphenyl, dehydroacetic acid, dibromohexamidine, 10-undecylenic acid, hexetidine, triclocarban, triclosan, 4-imidazolidinyl urea, 1-(4-chlorophenoxy)-1-(imidazole-1-yl)-3,3-dimethyl-2-butanone, 1,3-bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 2-benzyl-4-chlorophenol, chlorohexidine, hexamidine, 5-ethyl-1-aza-3,7-dioxabicyclo-[3.3.0]-octane, chlorphenesin, 3-iodo-2-propynyl butylcarbamate, and ethyl lauroyl arginate.

7. The method as set forth in claim 1, wherein the step (II) of adding the one or more preservatives to the base formulation comprises adding
   (a) at least one preservative selected from the group consisting of sorbic acid, 2-hydroxydiphenyl, 4-hydroxybenzoic acid, dehydroacetic acid, dibromohexamidine, 10-undecylenic acid, hexetidine, triclocarban, triclosanum, 4-chloro-3,4-dimethylphenol, imidazolidinyl urea, hexamethylenetetramine, 1-(4-chlorophenoxy)-1-(imidazole-1-yl)-3,3-dimethyl-2-butanone, 1,3-Bis-(hydroxymethyl)-5,5-dimethyl-2,4-imidazolidinedione, 1-hydroxy-4-methyl-6-(2,4,4-trimethylpentyl)-2-pyridone, bromochlorophene, 3-methyl-4-(1-methylethyl)phenol, 5-chloro-2-methyl-3(2H)-isothiazolone, 2-benzyl-4-chlorophenol, 2-chloroacetamide, chlorohexidine, 4, 4-dimethyl-1,3-oxazolidine, 1-phenoxy-propane-2-ol, hexamidine, 5-ethyl-1-aza-3,7-dioxabicyclo-[3.3.0]-octane, chlorphenesin, sodium hydroxymethyl amino acetate, benzyl hemiformal, 3-iodo-2-propynyl butylcarbamate, methylisothiazolinone, and ethyl lauroyl arginate, and
   (c) at least one preservative selected from the group consisting of sodium sulfite, sodium hydrogen sulfite, potassium hydrogen sulfate, zinc pyrithione, benzoic acid, salicylic acid, sorbic acid, formic acid, propionic acid, 2-phenoxy ethanol, benzyl alcohol, 1-phenoxy-propane-2-ol, isopropanol, and ethanol.

8. The method as set forth in claim 1, wherein the step (III) of adding the one or more oxidation dye precursors and/or direct dyes (b) to the base formulation comprises adding the at least one direct dye.

9. The method as set forth in claim 8, wherein at least one neutral direct dye is added as the direct dye.

10. The method as set forth in claim 8, wherein at least one cationic direct dye is added as the direct dye.

11. The method as set forth in claim 8, wherein at least one anionic acid dye is added as the direct dye.

12. The method as set forth in claim 1, wherein the step (III) of adding the one or more oxidation dye precursors and/or direct dyes (b) to the base formulation comprises adding the at least one oxidation dye precursor.

\* \* \* \* \*